US012674135B2

(12) United States Patent
Tomita et al.

(10) Patent No.: US 12,674,135 B2
(45) Date of Patent: Jul. 7, 2026

(54) THREE-DIMENSIONAL CULTURE OF IMMORTALIZED SKIN CELLS ON THE SUPERFICIAL LAYER OF WHICH A STRATUM CORNEUM IS FORMED, METHOD FOR PRODUCING SAID THREE-DIMENSIONAL CULTURE, AND METHOD FOR EVALUATING TEST SUBSTANCE USING SAID THREE-DIMENSIONAL CULTURE

(71) Applicant: National Institute of Advanced Industrial Science and Technology, Tokyo (JP)

(72) Inventors: Tatsunosuke Tomita, Tsukuba (JP); Yoshihiro Nakajima, Takamatsu (JP); Koyomi Miyazaki, Tsukuba (JP); Yoshihiro Ohmiya, Ikeda (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 975 days.

(21) Appl. No.: 17/794,575

(22) PCT Filed: Jan. 21, 2021

(86) PCT No.: PCT/JP2021/002020
§ 371 (c)(1),
(2) Date: Jul. 21, 2022

(87) PCT Pub. No.: WO2021/149761
PCT Pub. Date: Jul. 29, 2021

(65) Prior Publication Data
US 2024/0279606 A1 Aug. 22, 2024

(30) Foreign Application Priority Data
Jan. 22, 2020 (JP) ................................. 2020-008607

(51) Int. Cl.
*C12N 5/071* (2010.01)

(52) U.S. Cl.
CPC ......... *C12N 5/0629* (2013.01); *C12N 5/0626* (2013.01); *C12N 5/0698* (2013.01); *C12N 2510/04* (2013.01); *C12N 2513/00* (2013.01); *C12N 2533/10* (2013.01)

(58) Field of Classification Search
None
See application file for complete search history.

(56) References Cited

FOREIGN PATENT DOCUMENTS

| | | |
|---|---|---|
| JP | H0889239 A | 2/1999 |
| JP | 2010193822 A | 9/2010 |
| JP | 2018102186 A | 7/2018 |
| JP | 2019514370 A | 6/2019 |
| WO | 2012/002507 A1 | 8/2013 |
| WO | 2018/020970 A1 | 1/2019 |
| WO | 2021/149761 A1 | 7/2021 |
| WO | 02070729 A2 | 9/2022 |

OTHER PUBLICATIONS

Sporl et al., A Circadian Clock in HaCaT Keratinocytes, Feb. 2011, Journal of Investigative Dermatology vol. 131, Issue 2, pp. 338-348 (Year: 2011).*
Nakajima et al., Multicolor Luciferase Assay System: One-Step Monitoring of Multiple Gene Expressions with a Single Substrate, BioTechniques, 2005, 38: 891-894 (Year: 2005).*
Mertl et al., A dual luciferase assay for evaluation of skin sensitizing potential of medical devices, Molecular Biology Reports, 2019, 46:5089-5102 (Year: 2019).*
Jung et al., co-stimulation of HaCaT keratinization with mechanical stress and air-exposure using a novel 3D culture device, Scientific Reports, May 2016 (Year: 2016).*
Extended European Search Report, dated Feb. 5, 2024 for European Application No. 21743842.3, in 9 pages.
Natsch et al., "Reporter cell lines for skin sensitizing testing", Arch Toxicol, 2015, vol. 89, pp. 1645-1668.
Poumay et al., "A simle reconstructed human epidermis: preparation of the culture model and utilization in in vitro studies", Arch Dermatol Res 2004, vol. 296, pp. 203-211.
Inoue et al., "Developement of 3D imaging technique of reconstructed human epidermis with immortalized epidermal cell line", Experimental Dermatology, 2018, vol. 27, pp. 563-570.
Kimura et al., The performance of an in vitro skin sensitisation test, IL-8 Luc assay (OECD442E), and the integrated approach with direct peptide reactive assay (DPRA). The Journal of Toxicological Sciences, vol. 43, pp. 741-749 (2018).
Ozaki et al., Serum affects keratinization and tight junctions in three-dimensional cultures of the mouse keratinocyte cell line COCA through retinoic acid receptor-mediated signaling. Histochemistry and Cell Biology, vol. 151, pp. 315-326 (2019).
Kojima, In vtro assays (in vitro test) method utilized for safety assessment of chemical substances. Seibutsu-Kogaku Kaishi, vol. 95(8), pp. 455-460 (2007).
Schagat et al., Normalizing Genetic Reporter Assays:Approaches and Considerations for Increasing Consistency and Statistical Significance. Prometech Journal, No. 23, pp. 9-12 (2007).

(Continued)

*Primary Examiner* — Allison M Fox
*Assistant Examiner* — Marisol Ann O'Neill
(74) *Attorney, Agent, or Firm* — K&L Gates LLP; Brian J. Novak; Giorgios N. Kefallinos

(57) ABSTRACT

Provided is a three-dimensional culture of immortalized skin cells, comprising a plate-like substrate and a culture layered product of immortalized skin cells adhering to the surface of the plate-like substrate, in which the superficial layer of the culture layered product is composed of a stratum corneum. The three-dimensional culture can be produced as follows: immortalized skin cells are seeded on a top surface of a culture medium-impregnated plate-like substrate, and three-dimensional culture is performed while applying stress on a superficial layer of an immortalized skin cell layer formed by layering of the immortalized skin cells. The three-dimensional culture can be used to evaluate the sensitization of a test substance.

4 Claims, 11 Drawing Sheets

Specification includes a Sequence Listing.

(56) References Cited

OTHER PUBLICATIONS

Sadagurski et al., Insuline-like growth factor 1 receptor signaling regulates skin development and inhibits skin keratinocyte differentiation. Molecular and Cellular Biology, vol. 26, pp. 2675-2687 (2006).

Tomita et al. Development of novel skin sensitizing test with human keratinocyte cell line. AATEX, vol. 23 (supplement), pp. 126 (2018).

Cellbed, About cellbed, About cell culture protocol. [online] https://web.archive.org/web/20190816024238/http://www.cellbed-jp.com/qaf.htlm (Mar. 19, 2021).

International Search Report and Written Opinion, dated Mar. 30, 2021, for International Application No. PCT/JP2021/002020 filed on Jan. 21, 2021.

* cited by examiner

1. Place Cellbed with the side with cells facing up.

2. Fill the outside with medium.

3. Change media every 2 to 3 days.

Alvetex scaffold (insert type) with deep petri dish

Insert-type scaffold

Gas phase
Medium
Immortalized skin cells
Cellbed
Bottom of insert-type scaffold
Medium Petri dish

FIG. 7

| | K14 | Involucrin | Nucleus | Bright Field Image |
|---|---|---|---|---|
| Example 2 | | | | |
| Comparative Example 1 | | | | |

1  CONTROL
2  12.5% dibutylaniline
3  25% dibutylaniline
4  12.5%hexylsalicylate

FIG. 15

1, Control
2, HQ 20 uM
3, HQ 100 uM
4, HQ 200 uM

SEQUENCE LISTING

<160> NUMBER OF SEQ ID NOS: 2

<210> SEQ ID NO 1
<211> LENGTH: 600
<212> TYPE: DNA
<213> ORGANISM: homo sapiens

<400> SEQUENCE: 1

```
gtcaggaggg aggggaggga gacccgact ctgcagaagg cgctcgctgc gtgccccacg    60
tccgccgaac gcggggttcg cgacccgagg ggaccgcggg ggctgagggg aggggccgcg   120
gagccgcggc taaggaacgc gggccgccca cccgctcccg gtgcagcggc ctccgcgccg   180
ggttttggcg cctcccgcgg gcgccccct cctcacggcg agcgctgcca cgtcagacga   240
agggcgcagc gagcgtcctg atccttccgc ccggacgctc aggacagcgg cccgctgctc   300
ataagactcg gccttagaac cccagtatca gcagaaggac attttaggac gggacttggg   360
tgactctagg gcactggttt tctttccaga gagcggaaca ggcgaggaaa agtagtccct   420
tctcggcgat tctgcggagg gatctccgtg gggcggtgaa cgccgatgat tatataagga   480
cgcgccgggt gtggcacagc tagttccgtc gcagccggga tttgggtcgc agttcttgtt   540
tgtggatcgc tgtgatcgtc acttggtgag tagcgggctg ctgggctggc cggggctttc   600
```

<210> SEQ ID NO 2

<211> LENGTH: 5202
<212> TYPE: DNA
<213> ORGANISM: homo sapiens

<400> SEQUENCE: 2

```
agatacattt tttttgtaaa cattggagta aataatgcct aagtgtttta gaataaatct      60
aataaagaaa ttaggtctac acataatttt gttttacttt tttttttttt tcttgcgaca     120
ggctctctgt cacccaggct ggagtacagt ggcatgataa cagctccctg cagcctcgac     180
ctccctggct caagtgatct tcccacctca gcctcctgag tagctgggac tacaggcatg     240
caccaccacg cccggctaat atttgtatat ttttgtagag acagagtttc atcatgttgc     300
ccaggctagt cttgaactcc tgggctcaag tgctccacct gaattggcct tccaaattac     360
aggcatagcc accacagtga gccctttttt ttttttaata aatttaacaa agaaaagaaa     420
tagctacaag taaatattta cttttttttt tcatattgaa gattggctga tcttagcctt     480
tctaagtcct aataaaatgc ctgtttacac aactggtgtc ttcccctaaa cctaaacttc     540
aaacttcaaa ctccaaactc caccgatttg gatagtatta gaaatggcat tcatattaat     600
ggttatagta cattttttta catgtgaatg caaatggaat tgttaggcat taaaaaagaa     660
agcttatata gtggaagaaa ataaagcatc tagacataag ctttaagaga tctattgtgt     720
taatacagct ttactttttg agtggtaagc ttttaaaaag aaatgtggtg ctctaactcc     780
aggaaaagat aagggtgact gaagtgatag tctagaggaa aaagatgcag acatttactg     840
agtacctcca atgtgccagg tgccattctg ggcattttca ttatgtttcc tcatttaatt     900
ctcatggtga tcctttggaa ctgtgttatt ctcattttta cagatgaggt aactgagaga     960
cagtcagatt aaagaactgc ctatgattgt ttggctaata ataagtggag gggtgaggct    1020
tgaaggcagg tttgtcttat tccaacaccc atacataccc ttaaatttaa gttattctga    1080
cttgtgttgc tcaaatccaa tgtgttcagc tgtttgcttc tccaattacc aagattttc     1140 tttaaaaggt aggacacttt tggcaacacg aaccaacttt gctcagtatt gttataaact    1200
gttaactgga gacatttgaa tttggagatg gaactgaaat ggtcttgcgg tactagagaa    1260
gatcaagtta tcacataaac aaagtacaga gctgagaaca tattttaaat ctttccacta    1320
actctgactt ttattgacta aaattttagt gggcagtatg tttatgttta tgactcttaa    1380
cattaacaac atcgtaagtc aaactcacta atatatgtta agcattctgt ttatgattct    1440
tttaacctag aggattgttg agctgggact aatttcctca aatgggaaaa aaacccaggt    1500
gagagctgag actgctcctg agactgagaa aggcagctct gacgggatct cagattttag    1560
cagcaggagt tgaacaatgg gcatagaatc agcttgccca agatctcctg attaataaac    1620 catgaacaa gatttaaacc caagttcatt tcatttcaaa gctcatacca cattttgccc     1680
accatatttt gctttgttat atgactacaa cttagttcag gcttacaaaa aagtcctaat    1740
tctaaaattc ctatgcgtg ggtgggaggg gatttagatg attttgcata ggcaagaaac      1800
acccagtttc atggagtttg atggaagagt tatgtactaa tatgggaaaa gtagaggcca    1860
tctttgtctt tgttctttct tttttagacg ggagtctcgc tctttcaccc aggctggagt    1920
gcagtggcgc tatctcggct cactgcaagc tccgcctcct gggttcacgc cattctcctg    1980
cctcagcctc ctgagtagct gggactacag gcgcccgcca ccgctcccgg ctaattttt      2040 atattttcag tagagacggg gtttcaccgt gttagctaag atggtttgga tctcctgaac    2100
tcgtgatccg cccgcctcgg actcccaaag tgctgggatt acaggcttga gccaccgcgc    2160
ccggccgtct ttgttctttc ttgaactctt ccttttcttg ggtgatagac ttcgtcaacg    2220
```

-continued

```
tctaatgagg atatctaggt gctagtctct gctcatcaaa tgattcttat ggctcaggag      2280
ccgaatggga cgtaaataaa cagttaagtc tcatgaactc actttgcatt catctctaga      2340
agatgacaaa acatttgtat ttatgtgtag cgtggcactt tagttaaact ttgtacccca      2400
ctttgctcta ttttaaagca gaatatcctt aaaaaggata cttagtcctg cttttttttt      2460
tccgcctaag cccatttagt ccttctactc attatgcaag gactcaaatg gttatcttta      2520
cagaagtgag acaagataga atcaatgctc ttgtagtcac ttcatctttg tccattccca      2580
cttctgatgg agagggttct aggacataat gcactgaagg ttacattgtg agagatgaac      2640
aacatttgca aaagaggtct ttttgccttg gaaaggcttc attcttaaaa aaaaatgtga      2700
gcatcaaggt taagtagacc tcattagctc aaactttaag gatgatatca ggataaagtt      2760
gggcccatga gaagagaatg agaggggagat atagtgacat gaaaataagg aggaaaacga      2820
ggtgtctatg taagttgggc tcaccataaa tacaaaggca accgttaggg aaaagcaaag      2880
aagtctttgc acatcctcag aactctgaat gtcttagtga tgctgtatga gtgagtctta      2940
atgatagtga actgaatcag tcaagccagg ttgtgtccat atgagaatgt gtctttgcta      3000
aacatgccaa catcactgaa gcaaagaaac ttggagtttt ctttaagata taggtctttt      3060
ttacctatcc ggcccaagct ttctcttctt gtcactccat gcactgtgtt ccgtatgcta      3120
aatagtttga gaaacccaaa tgggccatgt tcgcctacat ttcattgtcc tgtacttcct      3180
gtcctgtact agcaaagcag tcccattggt ctttcttctc ctcattaaca ataaaggtaa      3240
cacttttgat gttgtttctt cagaaaacct tcattcatca aaactgcctc aaagatcatg      3300
tttgtttgat tccagaactt cctgtaatta cctgttattg taacactcat cactgtattt      3360
tacttacttg tgtaactaat tttccatatt ctgcactaga caacaaagtc ctttaagtca      3420
ggtactatat ctatttacat agcattcaca tctcctacaa taagggacat tagcagataa      3480
acaacacata ttaaatgaat aatgaagttt ctgaaatact acagttgaaa actataggag      3540
ctacattata tagaataaac atttactttg ctatagaatt cagtgtaacc caggcattat      3600
tttatcctca agtcttaggt tggttggaga aagataacaa aaagaaacat gattgtgcag      3660
aaacagacaa accttttttgg aaagcatttg aaaatggcat tcccctcca cagtgtgttc      3720 acagtgtggg caaattcact gctctgtcgt actttctgaa aatgaagaac tgttacacca      3780
aggtgaatta tttataaatt atgtacttgc ccagaagcga acagacttttt actatcataa      3840 gaacccttcc ttggtgctct ttatctacag aatccaagac ctttcaagaa aggtcttgga      3900 ttctttttctt caggacacta ggacataaag ccacctttttt atgatttgtt gaaatttctc      3960
actccatccc ttttgctagt gatcatgggt cctcagaggt cagacttggt gtccttggat      4020
aaagagcatg aagcaacagt ggctgaacca gagttggaac ccagatgctc tttccactaa      4080
gcatacaact ttccattaga taacacctcc ctcccacccc aaccaagcag ctccagtgca      4140
ccactttctg gagcataaac ataccttaac tttacaactt gagtggcctt gaatactgtt      4200
cctatctgga atgtgctgtt ctctttcatc ttcctctatt gaagccctcc tattcctcaa      4260
tgccttgctc caactgcctt tggaagattc tgctcttatg cctccactgg aattaatgtc      4320
ttagtaccac ttgtctattc tgctatatag tcagtcctta cattgctttc ttcttctgat      4380
agaccaaact cttttaaggac aagtacctag tcttatctat ttctagatcc cccacattac      4440
tcagaaagtt actccataaa tgtttgtgga actgatttct atgtgaagca catgtgcccc      4500
ttcactctgt taacatgcat tagaaaacta aatcttttga aaagttgtag tatgcccccct      4560
```

-continued

```
aagagcagta acagttccta gaaactctct aaaatgctta gaaaaagatt tattttaaat    4620
tacctcccca ataaaatgat tggctggctt atcttcacca tcatgatagc atctgtaatt    4680
aactgaaaaa aaataattat gccattaaaa gaaaatcatc catgatcttg ttctaacacc    4740
tgccactcta gtactatatc tgtcacatgg tactatgata aagttatcta gaaataaaaa    4800
agcatacaat tgataattca ccaaattgtg gagcttcagt attttaaatg tatattaaaa    4860
ttaaattatt ttaaagatca aagaaaactt tcgtcatact ccgtatttga taaggaacaa    4920
ataggaagtg tgatgactca ggtttgccct gaggggatgg gccatcagtt gcaaatcgtg    4980
gaatttcctc tgacataatg aaaagatgag ggtgcataag ttctctagta gggtgatgat    5040
ataaaaagcc accggagcac tccataaggc acaaactttc agagacagca gagcacacaa    5100
gcttctagga caagagccag gaagaaacca ccggaaggaa ccatctcact gtgtgtaaac    5160
atgacttcca agctggccgt ggctctcttg gcagccttcc tg                       5202
```

THREE-DIMENSIONAL CULTURE OF IMMORTALIZED SKIN CELLS ON THE SUPERFICIAL LAYER OF WHICH A STRATUM CORNEUM IS FORMED, METHOD FOR PRODUCING SAID THREE-DIMENSIONAL CULTURE, AND METHOD FOR EVALUATING TEST SUBSTANCE USING SAID THREE-DIMENSIONAL CULTURE

CROSS REFERENCE TO RELATED APPLICATIONS

This application is a national phase filing of PCT/JP2021/002020, filed on Jan. 21, 2021, which claims priority to Japanese Patent Application Number 2020-008607, filed on Jan. 22, 2020, the entire disclosures of each which are incorporated herein by reference.

REFERENCE TO A "SEQUENCE LISTING", A TABLE, OR A COMPUTER PROGRAM LISTING APPENDIX SUBMITTED IN ELECTRONIC FORM AND AN INCORPORATION-BY-REFERENCE OF THE MATERIAL

A Sequence Listing forms part of this application entitled "0818333-00111_Sequence_Listing.xml", created on Mar. 22, 2023, and 8,820 bytes in size, and is hereby incorporated by reference in its entirety.

TECHNICAL FIELD

The present disclosure relates to a three-dimensional culture of immortalized skin cells on the superficial layer of which a stratum corneum is formed, a method for producing the three-dimensional culture, and a method for evaluating a test substance using the three-dimensional culture.

This application claims the benefit of Japanese Patent Application No. 2020-8607, filed on Jan. 22, 2020, the entire disclosure of which is incorporated by reference herein.

BACKGROUND ART

Cultured skin cells are widely used in the development of cosmetics, pharmaceuticals, and quasi-drugs for screening test substances or the like having toxicity or skin protective activity or for elucidating their mechanisms. For example, there is a method in which skin cells are collected from a healthy adult and used for the above-described screening, but there is an ethical problem in receiving skin cells from a healthy adult for screening, and there is also a problem that skin characteristics vary depending on the skin donor.

On the other hand, there is an in vitro complete skin model using primary human fibroblasts as a skin model that does not rely on skin donation from healthy individuals (Patent Literature 1). This is an in vitro complete skin model including a support layer containing a collagen matrix, a dermal equivalent, a basement membrane, an epidermal equivalent, and the dermal equivalent or the epidermal equivalent includes a three-dimensional sweat gland equivalent. Specifically, primary fibroblasts are cultured to produce a dermal equivalent, primary keratinocytes are cultured on the dermal equivalent, and then further cultured at the air-culture medium boundary to form a three-dimensional sweat gland equivalent.

Similarly, there is a method in which human fibroblasts are cultured to form a support for cultured skin, melanocyte suspension is added and adhered to this support, and human epidermal keratinocytes are further seeded to form an epidermal layer and a stratum corneum layer by air-exposure culture (Patent Literature 2).

CITATION LIST

Patent Literature

Patent Literature 1: Unexamined Japanese Patent Application Publication (Translation of PCT Application) No. 2019-514370
Patent Literature 2: Unexamined Japanese Patent Application Publication No. 2010-193822
Patent Literature 3: International Publication No. WO2012/002507

SUMMARY OF INVENTION

Technical Problem

However, primary cultured cells such as primary human fibroblasts or primary keratinocytes used in the Patent Literature 1 has a finite lifespan. The same is true for normal human skin fibroblasts or normal human epidermal keratinocytes used in the Patent Literature 2. Introducing a reporter gene into cultured cells allows visualization of intracellular information (Patent Literature 3), however, even when a specific reporter gene is introduced into finite-lived cells, such as primary cultured cells, it is difficult to carry out long-term successive culture. Primary cultured cells are often not a single cell but a mixture of a variety of cells, and therefore, even when limited to a predetermined period of culture, maintenance of cellular characteristics is not ensured. Furthermore, primary human cells and other human cells are of a nature that requires ethical considerations, and when researchers are unable to collect such cells by themselves, it is necessary to purchase such cells from specific overseas companies.

On the other hand, immortalized skin culture cell lines have advantages such as the ability to be cultured successively and low variation among production lots. A reporter assay can be performed by introducing a reporter gene into skin culture cells using a genetic engineering technique. However, epidermal tissue in vivo is a three-dimensional structure composed of, from the deepest layer, a basal layer, a spinous layer, a granular layer, and a stratum corneum. In vitro cell culture usually yields only a two-dimensional monolayer in a container, and spontaneous formation of three-dimensional structures does not occur. In particular, normal in vitro culture of immortalized skin cell lines only results in division and proliferation of the same skin cells, and three-dimensional culture does not result in three-dimensional structures formed by different differentiated cells such as stratum corneum on the surface of a culture. Therefore, there is a desire to develop a technology to form a three-dimensional structure composed of immortalized skin cells that can be purchased and that has a layered structure like normal skin cell tissue.

Jurkat, U937 cells, THP-1 cells, and the like used in Patent Literature 3 are all immune cells, not skin cells. Although there are examples of reporter genes being introduced into these immune cells and other primary cultured cells, there are no examples of a reporter gene being introduced into immortalized skin cells and creating a three-dimensional structure while retaining the function of that reporter. From the viewpoint of protecting animals, it is desirable to develop a three-dimensional cultured skin model in which a reporter gene is introduced into immortalized skin cells and a stratum corneum is formed on the superficial layer for utilization in an alternative method to animal experiments for testing the efficacy and safety evaluation of various test substances without animal testing.

In view of the present situation described above, an objective of the present disclosure is to provide a three-dimensional culture of immortalized skin cells with a stratum corneum formed and a method for producing the same.

Another objective of the present disclosure is to provide a method for evaluating a test substance, in which immortalized skin cells into which a reporter gene has been introduced are used as a three-dimensional culture, and the test substance is administered to the immortalized skin cells to evaluate the skin sensitization and/or the physiological activity of the test substance based on the expression of the reporter gene introduced into the culture.

Solution to Problem

The present inventors found that a three-dimensional culture of immortalized skin cells with a stratum corneum formed on the superficial layer of a cell culture can be produced by three-dimensionally culturing immortalized skin cells while applying stress, and that such a three-dimensional culture can be suitably used for screening a test substance, thereby completing the present disclosure.

Specifically, the present disclosure provides a three-dimensional culture of immortalized skin cells, comprising a plate-like substrate and a culture layered product of immortalized skin cells adhering to a surface of the plate-like substrate, wherein a superficial layer of the culture layered product is composed of a stratum corneum.

The present disclosure provides the three-dimensional culture of the immortalized skin cells, wherein the immortalized skin cells are one or more selected from the group consisting of HaCaT, NHEK/SVTERT3-5 (human skin keratinocytes), SIK (Spontaneous immortalized epidermal keratinocytes), immortalized human epidermal keratinocytes-SV40, immortalized human melanocytes-hTERT, and immortalized human melanocytes-hTERT/SV40.

The present disclosure provides the three-dimensional culture of the immortalized skin cells, wherein the immortalized skin cells include a first reporter gene controlled by a stable expression promoter, a second reporter gene controlled by a promoter that can evaluate skin sensitization, and/or a third reporter gene controlled by a promoter that can evaluate physiological activity.

The present disclosure provides the three-dimensional culture of the immortalized skin cells, wherein the plate-like substrate is a liquid-impregnating substrate comprising one or more substrates selected from the group consisting of silica, alumina, zirconia, titania, hydroxyapatite, and a synthetic resin.

Furthermore, the present disclosure provides a method for producing a three-dimensional culture of immortalized skin cells with stratum corneum formed on a superficial layer thereof, wherein three-dimensional culture is performed while stress is applied to the immortalized skin cells.

The present disclosure provides the production method, wherein
the immortalized skin cells are seeded on a top surface of a culture medium-impregnated plate-like substrate, and the three-dimensional culture is performed while applying stress on a superficial layer of an immortalized skin cell layer formed by layering of the immortalized skin cells.

The present disclosure provides the production method, wherein
the immortalized skin cells are seeded on a bottom of an inner container whose bottom is culture medium-impregnated,
the inner container is stored in an outer container, and
in the outer container, three-dimensional culture is performed while applying stress on the superficial layer of the immortalized skin cell layer.

The present disclosure provides the production method, wherein
the three-dimensional culture while applying stress on the superficial layer of the immortalized skin cell layer is one or more of:
oligotrophic culture of the superficial layer of the immortalized skin cell layer;
anoxic culture of the superficial layer of the immortalized skin cell layer;
carbon dioxide-poor culture of the superficial layer of the immortalized skin cell layer;
humidity-poor culture of the superficial layer of the immortalized skin cell layer; or
culture of the superficial layer of the immortalized skin cell layer with enough culture medium not to dry out the superficial layer of the immortalized skin cell layer.

The present disclosure provides the production method, wherein the immortalized skin cells are one or more selected from the group consisting of HaCaT, NHEK/SVTERT3-5 (human skin keratinocytes), SIK (Spontaneous immortalized epidermal keratinocytes), immortalized human epidermal keratinocytes-SV40, immortalized human melanocytes-hTERT, and immortalized human melanocytes-hTERT/SV40.

The present disclosure provides the production method, wherein the immortalized skin cells include a first reporter gene controlled by a stable expression promoter, a second reporter gene controlled by a promoter that can evaluate skin sensitization, and/or a third reporter gene controlled by a promoter that can evaluate physiological activity.

The present disclosure provides a method for evaluating a test substance, wherein a test substance is administered to the three-dimensional culture of immortalized skin cells, and the skin sensitization and/or the physiological activity of the test substance are/is evaluated based on the expression levels of the second reporter gene and/or the third reporter gene with respect to the expression level of the first reporter gene.

Advantageous Effects of Invention

According to the present disclosure, a three-dimensional culture of immortalized skin cells is obtained. Since the superficial layer of this culture comprises a stratum corneum, such a culture can be used as a substitute for laboratory animals for evaluation of a physiologically active substance that maintains skin sensitization and skin health.

BRIEF DESCRIPTION OF DRAWINGS

FIG. 7 is a diagram showing results of K14 and involucrin immunostaining, nuclear Hoechst staining, and brightfield of a three-dimensional culture of HaCaT obtained in the culture of Example 2;

FIG. 8 is a diagram showing results of Comparative Example 2 and Example 4, and the results of multicolor luminescence measurements of red light-emitting luciferase (with IL-8 promoter) and green light-emitting luciferase (with UBC promoter) by the real-time luminescence monitoring system for cultured cells in a two-dimensional culture and a three-dimensional culture.

FIG. 15 is a diagram showing results of Example 8, showing the relative bioluminescence intensity of red light-emitting luciferase to green light-emitting luciferase.

DESCRIPTION OF EMBODIMENTS

Figure 1:
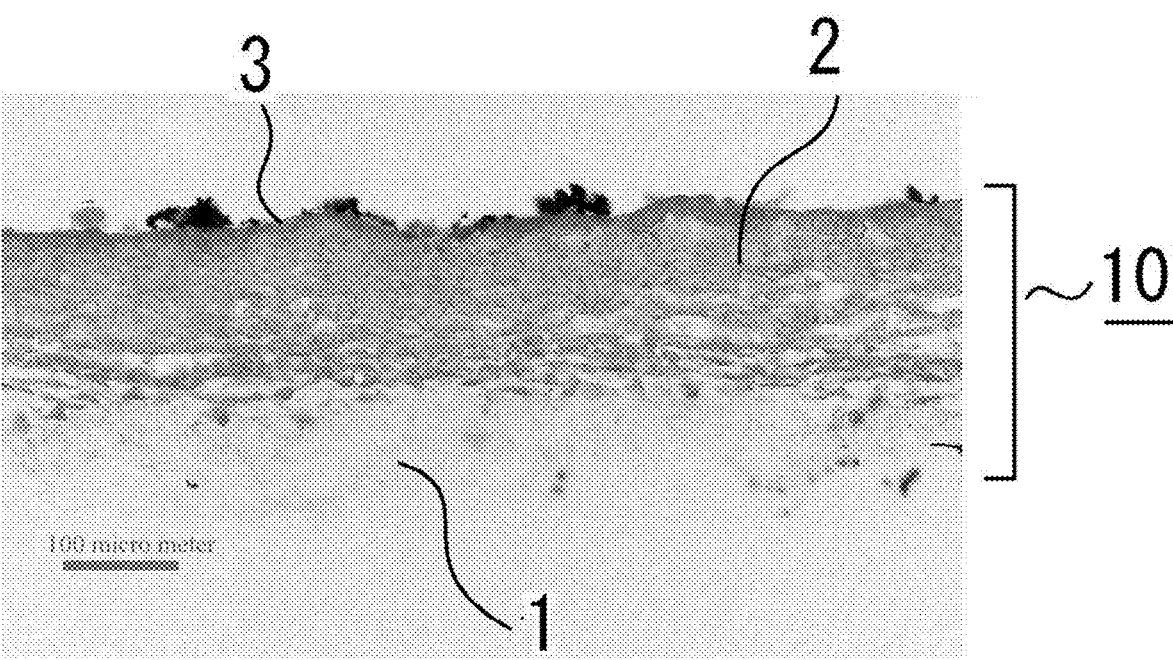
FIG. 1 is a diagram illustrating the three-dimensional culture of immortalized skin cells of the present disclosure, and shows one example of a longitudinal sectional view of a three-dimensional culture adhered to the surface of a plate-like substrate, where the superficial layer comprises a stratum corneum.

A first aspect of the present disclosure is a three-dimensional culture layered product of immortalized skin cells, comprising a plate-like substrate and a culture layered product of immortalized skin cells adhering to the surface of the plate-like substrate, wherein the superficial layer of the culture layered product is composed of a stratum corneum. FIG. 1 shows one example of a preferable aspect of a three-dimensional culture 10 comprising a plate-like substrate 1 and immortalized skin cells 2 adhered to the surface thereof, wherein a superficial layer 3 of a culture layered product of the immortalized skin cells 2 is a stratum corneum. Since this product is similar to the structure of biological skin epidermis, this can be used as an alternative skin tissue to animal experiments for screening of a variety of substances, such as skin sensitizers. In the present disclosure, a stratum corneum refers to a superficial layer of layered stratum corneum cells, and a stratum corneum cell means a cell that expresses at least cytokeratin 2.

The three-dimensional culture of immortalized skin cells of the present disclosure is not simply a cell culture layered product, and as described in Examples below, cytokeratin markers differed from layer to layer, with cytokeratin 10 being expressed particularly near the cell superficial layer, cytokeratin 14 being expressed particularly in subcellular layers, and cytokeratin 2 being present throughout the cell area. The cytokeratin 2 is a marker that is expressed in a stratum corneum in normal cells. At least the superficial layer of the three-dimensional culture of the present disclosure is a stratum corneum expressing cytokeratin 2, allowing screening of substances such as liposoluble compounds, which was not possible with conventional two-dimensional cultures. Moreover, since the immortalized skin cells 2 are adhered to the plate-like substrate 1, the three-dimensional culture 10 of the present disclosure can be easily transferred from one culture layered product to another by handling the plate-like substrate. In particular, by checking the plate-like substrate layer, it is easy to determine on which side the superficial layer of the three-dimensional culture is.

In the three-dimensional culture of the present disclosure, the plate-like substrate is preferably a liquid-impregnating substrate comprising one or more substrates selected from the group consisting of silica, alumina, zirconia, titania, hydroxyapatite, and a synthetic resin. Examples of the synthetic resin include polyethylene terephthalate, urethane, polypropylene, polyester, polystyrene, polycaprolactone, and poly-L-lactic acid. In the present disclosure, "liquid-impregnating" means a property that enables impregnation and retention of culture medium. For example, silica, alumina, zirconia, titania, hydroxyapatite, a non-woven fabric carrier made of synthetic resin processed into a fiber shape, a mesh carrier, or a porous plate-like material with pores formed therein are liquid-impregnating. In order for a culture layered product of immortalized skin cells to adhere to a plate-like substrate, the plate-like substrate is preferably a scaffold for cell culture. In order to achieve a suitable environment for such a scaffold, a plate-like substrate preferably has a porosity that allows cells to be seeded and cultured on the substrate. The plate-like substrate may further contain an extracellular matrix component such as hyaluronic acid, collagen, elastin, laminin, fibronectin, or poly-L or D-lysine. The thickness of a plate-like substrate is from 100 to 600 μm, and more preferably from 200 to 300 μm. Handling of a plate-like substrate in this range is easy. Cellbeds made of silica fiber manufactured by Japan Vilene Company, Ltd. can be suitably used as such a plate-like substrate.

Immortalized skin cells that can survive on a plate-like substrate can be widely used. For example, any of HaCaT, NHEK/SVTERT3-5 (human skin keratinocyte), SIK (immortalized epidermal keratinocyte by spontaneous immortalization), immortalized human epidermal keratinocytes-SV40, immortalized human melanocyte-hTERT, or immortalized human melanocyte-hTERT/SV40 can be used. HaCaT is preferably used. The three-dimensional culture of the present disclosure, stored in a container, can survive for a long period of time with a culture medium impregnated in a plate-like substrate.

The immortalized skin cells may further include a first reporter gene controlled by a stable expression promoter, a second reporter gene controlled by a promoter that can evaluate skin sensitization, and/or a third reporter gene controlled by a promoter that can evaluate physiological activity. The three-dimensional culture of the disclosure can be used for screening of a variety of substances as an alternative skin tissue to animal experiments, and by introducing luciferase genes or the like as a first reporter gene, a second reporter gene, or a third reporter gene, an effect of the screening can be visualized. In this case, when the expression level of the first reporter gene, which is regulated by a stable expression promoter, is used as an internal standard, the increase or decrease in the expression level of the second reporter gene or the third reporter gene can be evaluated relative to the first reporter gene.

As the stable expression promoter, a promoter originally possessed by immortalized skin cells may be used, or a promoter separately prepared may be used. Examples of the stable expression promoter include UBC (ubiquitin C), B2M (β-2-microglobulin), GAPDH, TK, SV-40, HPRT, β-actin, G6PDH, and EF (elongation factor). In the present disclosure. UBC, β-actin, or GAPDH is preferably used as a stable expression promoter. The number of stable expression promoters is not limited to one, and two or more promoters may be introduced into a cell.

Examples of a promoter that can evaluate skin sensitization include a gene promoter such as: IL-1beta, IL-4, IL-6, or IL-8, which is involved in hyperinflammation; IL-10, which, conversely, is involved in suppression: IL-17 or IL-22, which is particularly markedly elevated in chronic skin inflammatory diseases: IL-12, which promotes differentiation of T cells into Th1 cells; IFN-γ, which is induced by IL-2 or IL-12 and has a regulatory effect on inflammation; or HO-1, which is induced by a cytokine and oxidative stress. The number of promoters that can be introduced to evaluate skin sensitization is also not limited to one, and two or more promoters may be introduced into cells, and the number of promoters to introduce can be selected according to the type of immortalized skin cells. For example, IL-6, IL-8, or IL-10 is preferred for HaCaT. When the expression level of mRNA or protein for IL-8 or IL-6 is increased (especially significantly increased) when immortalized skin cells are in contact with a test substance as compared to when a test substance is not in contact, this test substance can be determined to have promoted the skin sensitization, and on the other hand, when the expression level of IL-8 or IL-6 decreases, the test substance can be determined to have suppressed skin sensitization. On the contrary, regarding IL-10, when the expression level of mRNA or protein for IL-10 is increased when immortalized skin cells are in contact with a test substance as compared to when a test substance is not in contact, this test substance can be determined to have suppressed the skin sensitization, and on the other hand, when the expression level decreases, the test substance can be determined to have promoted skin sensitization.

Examples of a promoter that can evaluate physiological activity include bmal1 or per2, which is a clock gene, filaggrin or keratin type10, which maintains skin health, and a tumor necrosis factor, TNF-alpha. The number of promoters introduced that can evaluate physiological activity is not limited to one, and two or more promoters may be introduced into cells, and which promoter is introduced may be selected according to the type of immortalized skin cells. Examples of HaCaT include bmal1, per2, filaggrin, and keratin10, and per2 and filaggrin are preferred. When immortalized skin cells are brought into contact with a test substance, the expression level of mRNA or protein of keratin10 or filaggrin is increased (especially significantly increased) compared to when a test substance is not in contact, the test substance can be determined to have stimulated physiological activity. On the other hand, when the expression level of keratin10 or filaggrin is decreased, the test substance can be determined to have suppressed the physiological activity.

Examples of such a promoter combination that can simultaneously evaluate skin sensitization and physiological activity include a combination of IL-8 and TNF-alpha and a combination of IL-6 and TNF-alpha in the case of HaCaT. Regarding NHEK/SVTERT3-5 cells, a combination of IL-8 and TNF-alpha or a combination of IL-6 and TNF-alpha is also a favorable example. Regarding SIK, a combination of IL-8 and TNF-alpha and a combination of IL-6 and TNF-alpha is also a favorable example.

Examples of the first reporter gene, the second reporter gene, and the third reporter gene used in the present disclosure include a luciferase gene, a fluorescent protein gene, and a coloring protein gene, and any of these may be used. For example, a luciferase gene can be used as the first reporter gene, a fluorescent protein gene can be used as the second reporter gene, and a colored protein gene can be used as the third reporter gene. On the other hand, for example, luciferase genes can be used as the first reporter gene, the second reporter gene, and the third reporter gene. In this case, luciferase genes may be detected by distinguishing signals that are expressed by any of the reporter genes. Examples of luciferase genes include a red luciferase and a green luciferase derived from *Phrixothrix*, an orange luciferase derived from *Rhagophthalmus ohbai*, and a green luciferase. A red luciferase derived from *Phrixothrix* is used as the first reporter gene, a green luciferase derived from *Phrixothrix* is used as the second reporter gene, and an orange luciferase derived from *Rhagophthalmus ohbai* is used as the third reporter gene, and when filters (color filters, bandpass filters, and the like) are used as appropriate, the emission amount of each emission wavelength can be measured separately.

When using a luciferase gene, it is preferable to use a luciferase that emits light with an emission wavelength that does not vary with measurement conditions such as pH and that can be mutually separated by color filters or the like. "Not vary with measurement conditions" means that the maximum emission wavelength varies by 3 nm or less when pH, temperature, concentration, and the like are changed. For example, for red and green luciferases derived from *Phrixothrix* and orange and green luciferases derived from *Rhagophthalmus ohbai*, the ratio of mutual light emission amounts except for green to green may be measured by using a filter. For example, when the maximum emission wavelengths are 20 nm or more, preferably 30 nm or more, more preferably 40 nm or more, and especially preferably 50 nm or more separate from each other, by using a filter with a wavelength between respective maximum wavelengths, measuring the transmittances of respective emissions before and after the filter, and converting the results, the emission amounts of respective emissions can be quantified at the same time. Examples of the luciferase used in the present disclosure include a green to red (maximum emission wavelength: from 535 to 635 nm) luciferase derived from *Phrixothrix*, an orange to green (maximum emission wavelength: from 530 to 600 nm) luciferase of *Pyrophorus*, and an orange to green (maximum emission wavelength: from 550 to 590 nm) luciferase of *Rhagophthalmus ohbai*.

Regarding the luciferase genes used in the present disclosure, each luciferase generated by expression of each reporter gene preferably emits light on the same light-emitting substrate. This is because quantitation of the emission amount from a plurality of luciferases can be performed at the same time, and the ratio of the expression levels of respective promoters can be precisely measured. For example, when using luciferases derived from *Phrixothrix, Rhagophthalmus ohbai*, or the like having a plurality of luciferases whose maximum emission wavelengths are separate from each other to some extent, by using one light-emitting substrate (for example, for luciferases derived from *Phrixothrix, Rhagophthalmus ohbai*, and *Pyrophorus*, a firefly luciferin can be used), the emission amounts derived from a plurality of luciferases coexpressed can be quantified at the same time.

A method for monitoring genes using a combination of luciferases, namely a *Phrixothrix* red luciferase for the first reporter gene and a *Rhagophthalmus ohbai* orange or green luciferase for the second reporter gene may be used. By monitoring using *Rhagophthalmus ohbai* green and orange luciferases as the second reporter gene and the third reporter gene, the three promoter activities can be measured at the same time. Red, orange, and green luciferases can be interchanged with each other.

A transgene is preferably incorporated into a vector and introduced into immortalized skin cells. A commercially available vector incorporating a second reporter gene controlled by a promoter that can evaluate skin sensitization and a third reporter gene controlled by a promoter that can evaluate physiological activity can also be used. A transgene may include a reporter gene, a promoter upstream of the reporter gene, as well as an element that enhances translation efficiency, an mRNA stabilizing element, an enhancer, IRES, SV40pA, or a drug resistance gene (such as Neor).

For the three-dimensional culture of the present disclosure used in screening for skin sensitization to induce dermatitis such as an eczema or a rash, for example, a three-dimensional culture of HaCaT in which UBC is introduced as a stable expression promoter, a green light-emitting luciferase gene is introduced as the first reporter gene, IL-8 is introduced as a promoter to evaluate skin sensitization, and a red light-emitting luciferase gene is introduced as the second reporter gene is preferably used.

For the three-dimensional culture used in screening for a physiological activity such as health maintenance of biological clock or keratinocytes, a three-dimensional culture of immortalized skin cells HaCaT in which bmal1 is introduced as a stable expression promoter, a green light-emitting luciferase gene is introduced as the first reporter gene, filaggrin is introduced as a promoter to evaluate a health maintenance function, and a red light-emitting luciferase gene is introduced as the second reporter gene is preferably used.

A second aspect of the present disclosure is a method for producing a three-dimensional culture of immortalized skin cells with stratum corneum formed on the superficial layer, wherein the immortalized skin cells are three-dimensionally cultured while applying stress on the immortalized skin cells. In the present disclosure, "three-dimensional culture" means use of a scaffold to form an aggregate of cells, and "three-dimensional culture" means a culture layered product having a thickness in the height direction.

In the immortalized skin cells used in the present disclosure, acquisition of "immortality" varies from cell line to cell line. For example, HaCaT is an immortalized human epidermal keratinocyte cell line established under $Ca^{2+}$ concentration and temperature conditions that differ from normal culture conditions, and NHEK/SVTERT3-5 is a human skin keratinocyte immortalized by hTERT and SV40. SIK is an immortalized epidermal keratinocyte by spontaneous immortalization, and immortalized human epidermal keratinocytes-SV40 is a human epidermal keratinocyte cell line that was created by successive passages of epidermal keratinocytes isolated from human skin and immortalized by introducing an SV40 large T antigen using lentiviral technology. SIK is useful in research focused on skin chemistry, including skin carcinogenesis. Immortalized human melanocytes-hTERT are immunized melanocytes, which are immortalized by successive passages of melanocytes isolated from human skin and transfected with an hTERT gene using lentiviral technology. This can be used to study skin diseases such as pigmentation (melanin formation) and melanoma. Furthermore, immortalized human melanocytes-hTERT/SV40 are a cell line created by successive passages of melanocytes isolated from human skin and immortalized by introducing an SV40 large T antigen and an hTERT gene using lentiviral technology. This can be used to study skin diseases such as pigmentation (melanin formation) and melanoma. However, the above-described immortalized cells are common in that the cells are single clones in which "differentiation" has been suppressed to allow for continuous culture. The present inventor, however, found that three-dimensional culturing of immortalized skin cells placed on a plate-like substrate while applying stress on the superficial layer of the immortalized skin cell layer formed by layering of the immortalized skin cells, and more specifically, that when a sufficient amount of culture medium is supplied to cells around the plate-like substrate and a very small amount of culture medium is supplied to the upper surface of a cultured cell layer, a three-dimensional culture in which stress is applied to the superficial layer cells due to the difference in the amount of culture medium present on the superficial layer and the superficial layer is differentiated into a stratum corneum.

Examples of the above-described three-dimensional culture performed while applying stress on a superficial layer of an immortalized skin cell layer include: oligotrophic culture, in which culture is performed while providing different amounts of nutrients to the superficial layer of an immortalized skin cell layer; anoxic culture, in which culture is performed while providing different amounts of oxygen: carbon dioxide-poor culture, in which culture is performed while providing different amounts of carbon dioxide; humidity-poor culture, in which culture is performed while providing different amounts of humidity; and culture of charging a culture medium to the extent that the surface cells do not dry out, while providing a difference in the amount of nutrients supplied and the amount of humidity supplied.

For example, a method using a culture medium-impregnated plate-like substrate as a scaffold, seeding immortalized skin cells on the top surface of the scaffold, and three-dimensionally culturing the immortalized skin cell layer while applying stress on the superficial layer of the immortalized skin cell layer may be used. More specifically, a method in which immortalized skin cells are seeded on the bottom of an inner container whose bottom is impregnated with a culture medium, and this inner container is then stored in an outer container for culture may be used. The bottom of an inner container may be made of a mesh structure through which a culture medium can pass, and a culture medium-impregnated plate-like substrate may be placed on top of the mesh to serve as the inner container. A culture medium-impregnated plate-like substrate is pre-impregnated with a culture medium and immortalized skin cells are seeded on top of the substrate. The inner container containing the immortalized skin cells is stored in the outer container, and then the outer container is charged with the culture medium and culture is performed. When cultured in this state, the culture medium-impregnated plate-like substrate serves as a scaffold to form a culture layered product with immortalized skin cells growing in layers inside the inner container. In the present disclosure, when forming a culture layered product, the amount of a culture medium in an outer container is adjusted to the extent that the superficial layer of an immortalized skin cell layer in an inner container does not dry out. The immortalized skin cells on and near the culture medium-impregnated plate-like substrate are supplied with a sufficient amount of a culture medium, while the immortalized skin cells on the superficial layer are not supplied with a sufficient amount of nutrient solution and are cultured in an oligotrophic state. This poor nutrition causes stress, and immortalized skin cells, whose differentiation was originally inhibited, differentiate into a stratum corneum. After immortalized skin cells are cultured to form from 3 to 10 cell layers, stress may be applied to the superficial layer to form a stratum corneum on the superficial layer.

The culture medium may be selected from among those suitable for two-dimensional culture of immortalized skin cells. D-MEM, KBM Basic Medium (Lonza), Kerationocyte Basal Medium 2 (TaKaRa), Human Epivita Growth Medium-Basic Medium (Toyobo), or the like can be preferably used as a culture medium. The culture medium may include insulin, bovine pituitary extract, human epidermal growth factor, adrenaline, transferrin, hydrocortisone, cholera toxin, fetal bovine serum, or a Ca ion such as $CaCl_2$). For example, when the stress is oligotrophic culture, in addition to change in the amount of a culture medium described above, the outer container may be charged with a culture medium used in two-dimensional culture, and a culture medium with a lower concentration of one or more components of this culture medium may be used as a culture medium to be provided from the surface of the cells. When a culture medium for two-dimensional use is used as it is in the outer container, for example, a culture medium obtained by diluting twice to five times is provided from the superficial layer to perform culturing. In the case of anoxic culture, in which the culture is performed while providing a difference in the amount of oxygen supplied, the outer container is supplied with a usual amount of oxygen, and the inner container is kept in a gas phase with a low oxygen concentration of from 10 to 50% of the amount of oxygen supplied to the outer container. The same is true for carbon dioxide-poor culture in which the culture is provided with a difference in the amount of carbon dioxide supplied, and the inner container is kept in a gas phase with a concentration of from 10 to 50% of the amount of carbon dioxide supplied to the outer container. In the case of humidity-poor culture, in which culture is performed while providing a difference in the humidity supplied, a method of supplying an atmosphere of from 5 to 50% of the humidity of the outer container to the cell surface of the inner container can be exemplified. In the present disclosure, the culture method may be a combination of these methods.

Culture is usually performed at from 30 to 40° C. for 5 to 40 days, preferably from 18 to 23 days, depending on the method of applying stress. A plate-like substrate desirably has pore diameters of about from 5 to 20 μm. This allows for production of a three-dimensional culture that is close to the original skin structure. In particular, since at least the superficial layer of a resulting three-dimensional culture is a stratum corneum expressing cytokeratin 2 or a cell layer close thereto, evaluation of a water-insoluble substance, which has been unfeasible with conventional two-dimensional culture, is also feasible.

The reason why a culture layered product of immortalized skin cells expresses different cytokeratin markers in different layers by the production method of the present disclosure, or why cytokeratin 2 is expressed at least in the superficial layer and differentiates into a stratum corneum or cells that approximate a stratum corneum is unknown. However, as shown in Examples described below, when a resulting three-dimensional culture was used for a sensitizing test with a lipophilic substance, the culture showed a greater sensitization result than a solvent control, resulting in a culture layered product with an affinity for the lipophilic substance. In contrast, a two-dimensional culture obtained by culturing immortalized skin cells on a coverglass did not show expression of cytokeratin 2.

Immortalized skin cells may have a first reporter gene controlled by a stable expression promoter, a second reporter gene controlled by a promoter that can evaluate skin sensitization, and/or a third reporter gene controlled by a promoter that can evaluate physiological activity. A first reporter gene, a second reporter gene, and a third reporter gene controlled by a stable expression promoter used in the production method of the present disclosure to be used can be the same as described above for the three-dimensional culture of immortalized skin cells. Examples of these reporter genes include a luciferase gene, a fluorescent protein gene, and a colored protein gene, and from the viewpoint of the ability to distinguish and detect signals from two or more, preferably three or more, reporter genes, a luciferase gene is preferred. A three-dimensional culture of immortalized skin cells in which a reporter gene has been introduced produced in the present disclosure is one in which all cells in which the reporter gene has been introduced are proliferated. In particular, since the superficial layer is a stratum corneum, the culture can be used for a reporter assay during screening of a test substance as an alternative to animal testing.

A third aspect of the present disclosure is a method for evaluating a test substance, in which the test substance is administered to a three-dimensional culture of immortalized skin cells into which a first reporter gene controlled by a stable expression promoter, and a second reporter gene controlled by a promoter that can evaluate skin sensitization and/or a third reporter gene controlled by a promoter that can evaluate physiological activity are introduced, and the skin sensitization and/or the physiological activity of the test substance are/is evaluated based on the expression levels of the second reporter gene and/or the third reporter gene with respect to the expression level of the first reporter gene.

Since a culture layered product of immortalized skin cells is adhered to the surface of a plate-like substrate in a three-dimensional culture to be used, this culture is stored in a culture container and pre-cultured, usually for 3 to 8 hours, and more preferably for 4 to 6 hours. Thereafter, after a test substance is added to or in contact with the three-dimensional culture for a predetermined period of time, the expression level of the first reporter gene, and the expression level of the second reporter gene and/or the third reporter gene are measured over time while the three-dimensional culture is cultured as is. The expression level of each reporter gene can be measured by measuring the luminescence or fluorescence of each reporter gene over time for a predetermined period of time using a real-time luminescence monitoring system for cultured cells or the like.

When the first reporter gene controlled by a stable expression promoter, and the second reporter gene and/or the third reporter gene controlled by a promoter whose skin sensitization and/or bioactivity can be evaluated are introduced into immortalized skin cells, skin sensitization and/or physiological activity affecting the expression levels of the second reporter gene and/or the third reporter gene can be easily and precisely evaluated by calculating the relative ratio using the expression level of the first reporter gene as an internal standard. When using immortalized skin cells into which the second reporter gene regulated by a promoter involved in skin sensitization and the third reporter gene that is regulated by a promoter related to the physiological activity with an effect of maintaining skin health are introduced, the skin sensitization and physiological activity of the test substance can be evaluated at the same time.

When evaluating a test substance, additional stimulation with a second test substance may be added after treatment of the test substance, and then the expression of each reporter gene may be evaluated. Examples of such a second test substance include PMA, Ionomycin, LPS, and an active oxygen production inhibitor (N-acetyl-cysteine). This evaluation method enables high-throughput evaluation of skin sensitization to an immunosuppressive drug such as dexamethasone or cyclosporine, an environmental pollutant such as a diesel engine exhaust particulate or formalin, or a sensitizer such as dinitrochlorobenzen or nickel.

EXAMPLES

Hereinafter, the present disclosure is described in more detail by way of Examples. However, the present disclosure is not limited thereto.

Example 1

A Cellbed 24-well carrier (JAPAN VILENE COMPANY, LTD.: made of silica fiber) was placed in each well of a 24-well plate (JAPAN VILENE COMPANY, LTD.) and hydrophilized with PBS. Thereafter, 500 µL of D-MEM suspension of HaCaT (containing 10% FBS and antibiotics, cell concentration: $1 \times 10^6$ cells/mL) was placed in each well and cultured for 3 hours at 37° C., 5% $CO_2$, and 100% humidity atmosphere.

Figure 2:
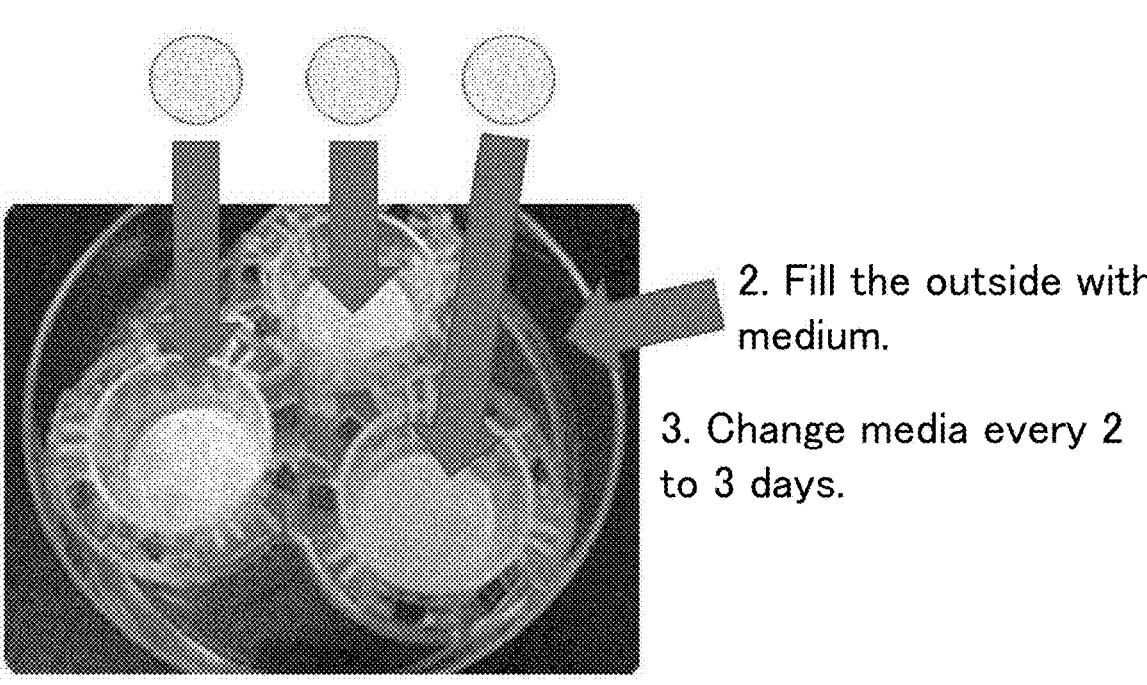
FIG. 2 is a diagram illustrating processes in Example 1, showing three well inserts with Cellbeds in an Alvetex, scaffold well insert deep petri dish, and the operating procedure.
Figure 3:
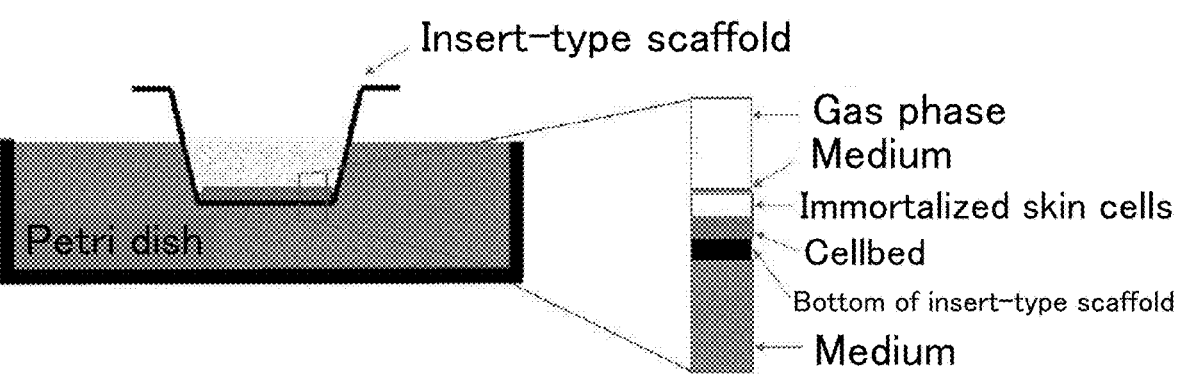
FIG. 3 is a diagram illustrating Example 1 and illustrating the relationship between a Petri dish, the bottom of a well insert, a Cellbed, immortalized skin cells, and culture medium during culture.

The above-described Cellbed to which a culture of HaCaT cells was to be adhered was placed with the surface to which the cells were to be adhered on top of a scaffold of Alvetex scaffold well insert type (for 12 wells) with as little D-MEM as possible brought into the well. No air bubbles were allowed between the scaffold and the Cellbed during placement. As shown in FIG. 2, an Alvetex scaffold well insert deep Petri dish was used to store three well inserts with the Cellbeds placed thereon, and 37 mL of KGM Gold culture medium (Lonza) was added to the Petri dish. An additional 50 µL of KGM Gold was added to the top surface of each Cellbed stored in the Petri dish, and three-dimensional culture was performed at 37° C. 5% $CO_2$, and 100% humidity. In this case, the bottom of the insert-type scaffold was completely submerged in the culture medium, but the Cellbed was not submerged in the culture medium, and from 50 to 150 µL of a culture medium was added to the Petri dish in such a manner that the top surface of the Cellbed was maintained wet with the culture medium. A layer of less than 1 mm of HaCaT cell culture medium was allowed to form on the top surface of the Cellbed. The culture medium in the Petri dish was changed every from 2 to 3 days, 18.5 mL at a time, and the culture was continued for 25 days. Each time the culture medium was changed, the Cellbed did not submerge in the culture medium, and the top surface of the Cellbed to which the HaCaT cells were adhered remained wet with the culture medium. A longitudinal end face during this culture is schematically shown in FIG. 3. The HaCaT cells were cultured in an environment of stress, where there was a culture medium around the cells and the cells were not immersed in the culture medium.

Figure 4:
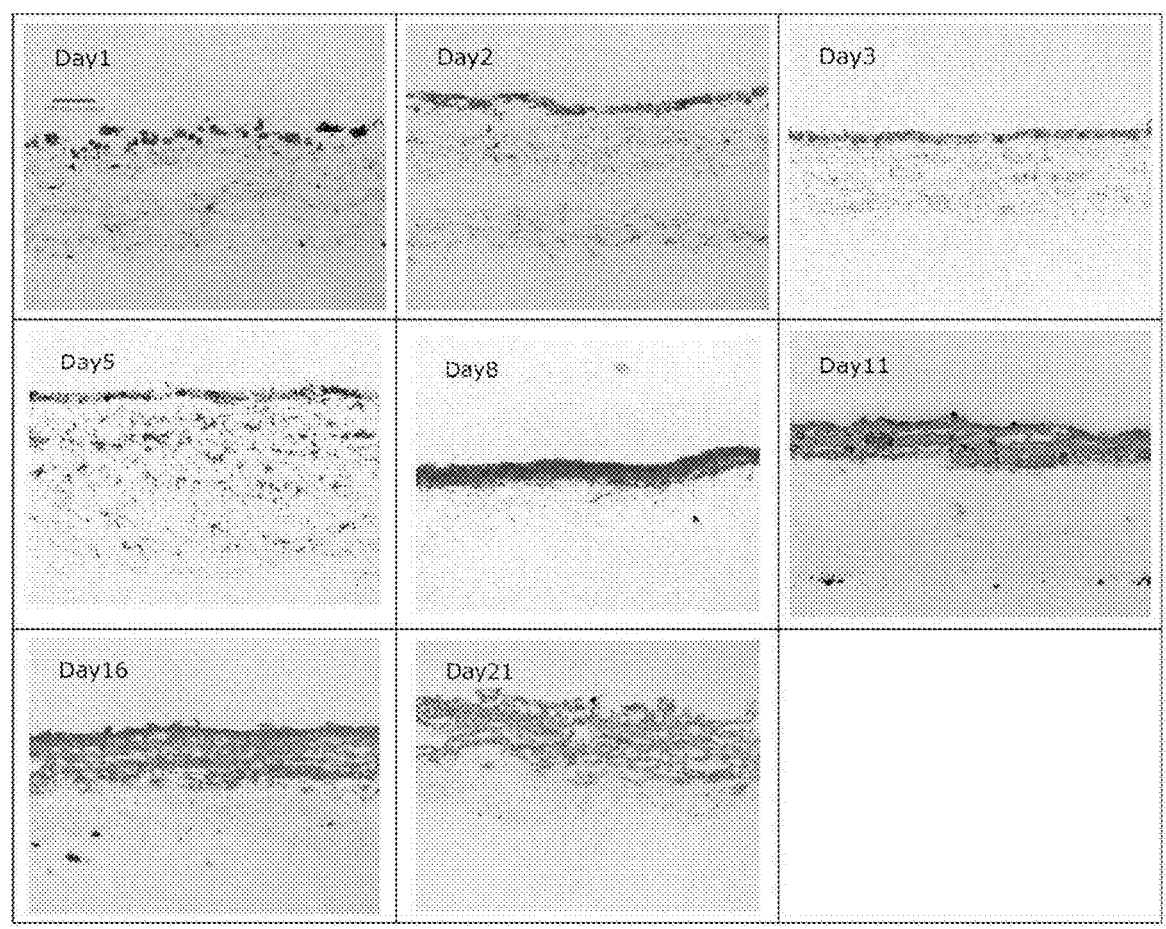
FIG. 4 is a diagram showing results of observation of cultured cells of Example 2 over time.

Staining with neutral red was performed to observe cell proliferation from day 1 to day 21 of culture. Three-dimensionally cultured cells on the Cellbed were rinsed once with PBS and then stained by immersion m neutral red solution for 5 minutes. After staining, the cells were rinsed with PBS three times and then immersed in 4% paraformaldehyde/PBS overnight and fixed. Fixed cells were embedded in OTC compound and sections were obtained by cutting lengthwise into 20 µm wide sections in a cryostat and examined under a microscope. Results of microscopy examination of cultures grown from day 1 to day 21 over time from the start of three-dimensional culture are shown in FIG. 4, using the method described above. Neutral red is a soluble dye and can be taken up intracellularly only by living cells. As shown in FIG. 4, dark immortalized skin cells adhering to the Cellbed, shown in light color, proliferated in layers over time in three-dimensional culture, resulting in three-dimensional cultures.

Example 2

Figures 5, 6:
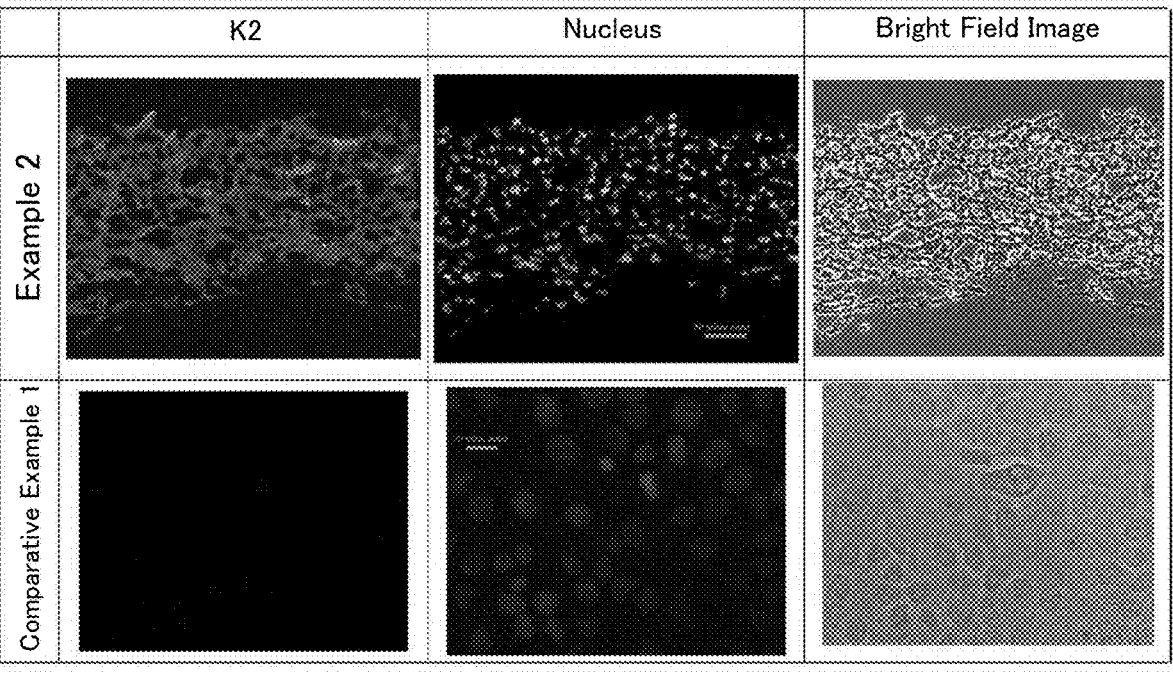
FIG. 5 is a diagram illustrating results of K2 immunostaining, nuclear Hoechst staining, and brightfield of a three-dimensional culture of HaCaT obtained in the culture of Example 2.
FIG. 6 is a diagram showing results of K10 immunostaining, nuclear Hoechst staining, and brightfield of a three-dimensional culture of HaCaT obtained in the culture of Example 2.

HaCaT cells were cultured for 25 days as in Example 1, and a three-dimensional culture of HaCaT cells was obtained. In this three-dimensional culture, the cell bed is a plate-like substrate to which a HaCaT culture layered product adhered in a layered fashion. This three-dimensional culture was rinsed with PBS three times and then immersed in 4% paraformaldehyde/PBS overnight and fixed. Fixed cells were treated with de-paraformaldehyde in retrieval buffer, embedded in an OTC compound, and cut lengthwise in a cryostat at a width of 5 µm. Obtained sections were then subjected to immunostaining and Hoechst staining. Immunostaining was performed using anti-Cytokeratin 2 rabbit antibody, anti-cytokeratin 10 rabbit antibody, and anti-cytokeratin 14 rabbit antibody as primary antibodies and Alexa488 conjugated anti-rabbit antibody as a secondary antibody. Obtained sections were stained with anti-involcurin mouse antibody and involcurin was detected using Alexa568-conjugated anti-mouse antibody as a secondary antibody. Hoechst staining was performed using Terumo NucBlue reagent and nuclei were detected. Stained sections were examined under a microscope using respective excitation lights. Results are shown in the top rows of FIGS. 5, 6, and 7, respectively. In FIGS. 5 to 7, a light-colored layer beneath dark-colored cells is a cell bed that corresponds to a plate-like substrate.

The top row of FIG. 5 shows cytokeratin 2 (K2), nuclei, and brightfield results; the top row of FIG. 6 shows cytokeratin 10 (K10), nuclei, and brightfield results; and the top row of FIG. 7 shows cytokeratin 14 (K14), involcurin, nuclei, and brightfield results.

The brightfield tissue shown in the top row of FIG. 5 comprised a large number of nuclei by Hoechst staining, confirming that the three-dimensional culture was a layered product of cells. The cells were found to express K2 by immunostaining. Expression of K10 was confirmed by immunostaining, especially in the surface area, as shown in the top row of FIG. 6, and expression of K14 and involcurin was confirmed by immunostaining, as shown in the top row of FIG. 7. K2 is expressed in all epithelial cells including the stratum corneum in normal skin tissue, K10 is expressed in the spinous layer, K14 is expressed in basal cells, and involucrin is expressed from the spinous layer to the superficial layer. In the three-dimensional culture obtained in Example 1, K2 is expressed throughout the structure, and K14 is widely expressed from the upper to the lower layers, and especially strongly expressed in the lowest layer. K10 was strongly expressed in the upper superficial layer, suggesting that the cells were differentiating into keratinocytes. Involucrin was found to be expressed throughout and densely expressed in the lower layers. The three-dimensional culture obtained in Example 1 was a culture of immortalized skin cells, HaCaT, and was a cell layered product that resembled the epidermal cell layer, containing a variety of keratinocytes found in normal cells and containing a large amount of involucrin in the lower layers.

Comparative Example 1

One ml of D-MEM used in Example 1 was dropped onto a cover glass, and 7×104 HaCaT were seeded thereon and cultured at a temperature of 37° C., 5% CO2, and 100% humidity. For convenience of description, a culture obtained from a three-day culture is referred to as a two-dimensional culture. Three days after culture, a three-dimensional culture was fixed with paraformaldehyde and subjected to immunostaining and Hoechst staining. Results are shown in the bottom rows of FIGS. 5, 6, and 7, respectively. The bottom row of FIG. 5 shows cytokeratin 2 (K2), nuclei, and brightfield results; the bottom row of FIG. 6 shows cytokeratin 10 (K10), nuclei, and brightfield results; and the bottom row of FIG. 7 shows cytokeratin 14 (K14), involcurin, nuclei, and brightfield results.

As shown in the bottom row of FIG. 5, cytokeratin 2 (K2), expressed in the superficial layer, could not be confirmed. As shown in the bottom row of FIG. 6, K10, which should be expressed in the spinous layer, expressed sparsely, while involucrin, also expressed in the spinous layer to the surface, was barely expressed, as shown in the bottom row of FIG. 7. On the other hand, K14, which is expressed in the basal layer, was well expressed. Comparing these expression profiles with the three-dimensional culture of Example 2, the cells comprising the three-dimensional culture expressed cytokeratin 2, which is characteristic of the stratum corneum, and showed a highly differentiated and keratinized surface with the characteristics of normal skin tissue.

Example 3

Micronuclei containing mouse artificial chromosome vector were isolated from CHO-K1 cells carrying a mouse artificial chromosome vector according to the usual method. The micronuclei were introduced into HaCaT cells using polyethylene glycol for micronuclear cell fusion, and then HaCaT cells into which the mouse artificial chromosome vector was introduced were selected using hygromycin.

According to a conventional method, a vector in which the HS4 insulator sequence was arranged upstream and downstream of and at the linkage of both cassettes of the IL-8 promoter sequence and the red light-emitting luciferase sequence and the ubiquitin C promoter sequence shown in SEQ ID NO:1 and the green light-emitting luciferase sequence was prepared. This was introduced into HaCaT cells carrying the mouse artificial chromosome vector described above by the lipofection method. Reporter vector-transfected cells were selected by selective culture using G418. SEQ ID NO:1 is the 601 nucleotide sequence from 4891 to 5491 of the ubiquitin C promoter (NCBI sequence ID NG_027722). The IL-8 promoter sequence used was the 8th to 5202 nucleotide sequence site of NCBI sequence ID NG_029889.1, shown in SEQ ID NO:2. This resulted in HaCaT with a red luciferase gene controlled by the IL-8 promoter and a green light-emitting luciferase controlled by the ubiquitin C promoter.

The thus obtained HaCaT was used to obtain a three-dimensional culture by the same method as in Example 1. The three-dimensional culture was a three-dimensional culture in which a Cellbed was used as a plate-like substrate as in Example 1, to which a HaCaT culture layered product was adhered, and the superficial layer of the three-dimensional culture was the stratum corneum.

Example 4

Three-dimensional culture obtained in Example 3 was placed in three 24-well plates for cell culture with black walls and transparent, colorless bottom one by one, and 1 mL of D-MEM containing 10% FBS, antibiotic [penicillin (100 U/mL)/streptomycin (0.1 mg/mL)] 0.2 mM luciferin potassium salt was placed therein.

Figures 8A, 8B:
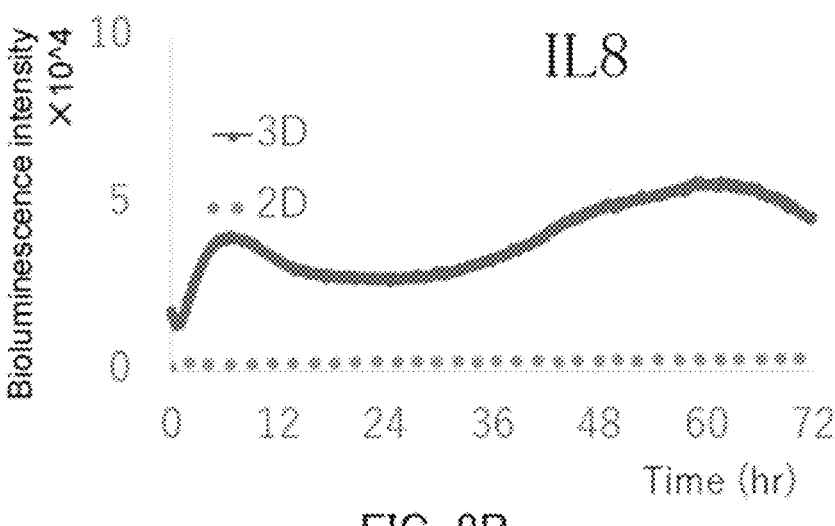
FIG. 8A illustrates bioluminescence intensity by red light-emitting luciferase (with IL-8 promoter)
FIG. 8B illustrates bioluminescence intensity by green light-emitting luciferase (with UBC promoter)

In order to evaluate the emission intensity of the three-dimensional structure, plastic paraffin film was sprinkled around this well plate and the luminescence was measured with a real-time luminescence monitoring system for cultured cells, Kronos HT (manufactured by ATTO Corporation). Measurement was performed using the color separation method shown in Reference 3, with and without an optical filter to separate red and green, for 10 seconds each, and continued for 72 hours in each well. The results of the multicolor luminescence measurements are shown in FIG. 8. FIG. 8A shows the bioluminescence of red light-emitting luciferase (IL-8 promoter), and FIG. 8B shows the bioluminescence of green light-emitting luciferase (UBC promoter). FIG. 8 also shows results of Comparative Example 2. In FIG. 8, the curve shown in 3D is the result of Example 4 (three-dimensional culture) and the curve shown in 2D is the result of Comparative Example 2 (two-dimensional culture).

Comparative Example 2

HaCaT with a red light-emitting luciferase gene controlled by the IL-8 promoter and a green light-emitting luciferase gene controlled by the ubiquitin C promoter prepared in Example 3 was placed in three 24-well plates for cell culture with black walls and transparent, colorless bottom each with 2×10$^5$ cells, and 1 mL of D-MEM containing 10% FBS, antibiotic [penicillin (100 U/mL)/streptomycin (0.1 mg/mL)] 0.2 mM luciferin potassium salt was placed therein.

As in Example 4, plastic paraffin film was sprinkled around this well plate and the luminescence was measured with a real-time luminescence monitoring system for cultured cells. Kronos HT (manufactured by ATTO Corporation). Measurement was performed with and without an optical filter for 10 seconds each, and continued for 72 hours in each well. The results of the multicolor luminescence measurements are shown in FIG. 8.

(Results)

Example 4 and Comparative Example 2 enable comparison of the emission intensity of red light-emitting luciferase (IL-8 promoter) and green light-emitting luciferase (ubiquitin C promoter) in the presence of cells in two-dimensional culture on the entire bottom surface of a 24-well plate and in the presence of a three-dimensional culture structure. As shown in FIG. 8, the three-dimensional culture (3D) resulted in higher emission intensity of red light-emitting luciferase (IL-8 promoter) and green light-emitting luciferase (ubiquitin C promoter) than that of the two-dimensional culture (2D). In particular, red light-emitting luciferase (IL-8 promoter), which emits light under the influence of sensitizers, showed stronger emission intensity in 3D than in 2D, suggesting that the layering of cells caused functional changes in the cells that increased their emission.

Example 5

Using the three-dimensional culture obtained in Example 3, the response to hydroquinone (HQ) as a hydrophilic sensitizer was evaluated.

A cell culture insert (Falcon Culture Insert #353095) comprising a clear, colorless, PET membrane with a 0.4 μm pore size bottom for 24 wells was inserted into the wells of a 24-well plate for cell culture with black walls and a colorless bottom, the three-dimensional culture was placed in the bottom of the culture insert with the cells on top, and 0.8 mL of KGM-gold containing 0.2 mM luciferin potassium salt was placed in the well outside the culture insert. For sensitization evaluation, a test substance was loaded from the top of the three-dimensional culture inside the insert. HQ was dissolved in KGM medium at 200 μM, 800 μM, and 2 mM, and 30 μL of each solution was loaded only from the top of the three-dimensional culture. As a solvent control, 30 μL of KGM medium was added from the top of the three-dimensional culture. Plastic paraffin film was sprinkled around this well plate and the luminescence was measured for 0 to 72 hours with a real-time luminescence monitoring system for cultured cells, Kronos HT (manufactured by ATTO Corporation). Measurements were taken every minute for 10 seconds for each color and continued for 0 to 72 hours.

Figure 9:
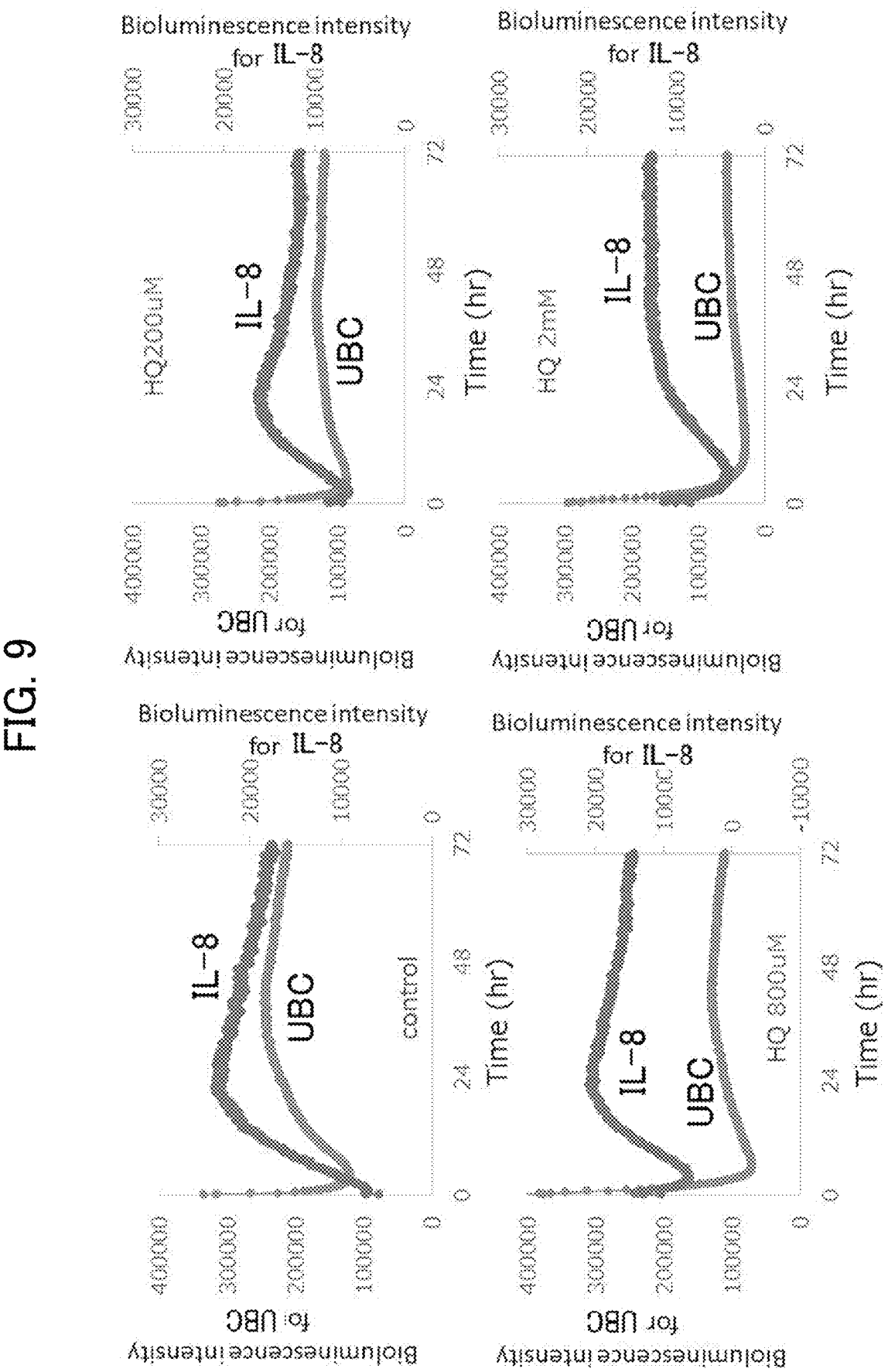
FIG. 9 is a diagram showing results of loading hydroquinone (HQ) in Example 5, in which the luminescence of red light-emitting luciferase and green light-emitting luciferase was measured for 72 hours by a real-time luminescence monitoring system for cultured cells.
Figure 10:
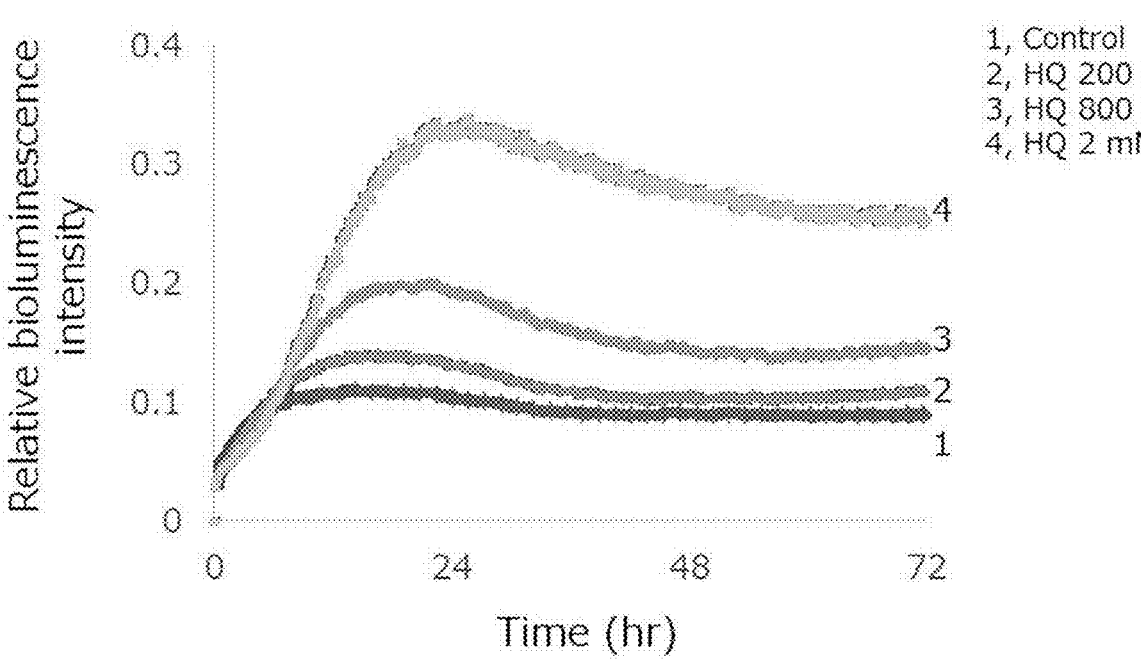
FIG. 10 is a diagram showing results of loading HQ in Example 5, showing the relative bioluminescence intensity of red light-emitting luciferase to green light-emitting luciferase.

Measurement results of HQ up to 72 hours are shown in FIG. 9. In FIG. 9, IL-8 indicates the luminescence of red light-emitting luciferase in samples and controls administered various concentrations of HQ, and UBC indicates the results of green light-emitting luciferase (ubiquitin C promoter). The emission of red light-emitting luciferase is a direct indicator of the response to skin sensitization by a test substance, while the ubiquitin C promoter, selected as a housekeeping gene, is an indicator that reflects cell viability. FIG. 10 shows the relative bioluminescence intensity of red light-emitting luciferase (IL-8 promoter) to green light-emitting luciferase (ubiquitin C promoter) in samples treated with various concentrations of the test substance and controls up to 72 hours of measurement (plotted at each point mean+/−SD with n=3, respectively). The relative bioluminescence intensity can be evaluated as a numerical value that corrects for an effect such as cell death due to toxicity.

As shown in FIG. 10, HQ, a hydrophilic sensitizer, showed a concentration-dependent increase in relative bioluminescence intensity in the range of from 200 UM to 2 mM concentration. Moreover, the method of Example 5 is to load a test substance from the top surface of a three-dimensional culture. This is a method that approximates, for example, a sensitization test to evaluate allergic reactions in a living body. It was found that the three-dimensional culture of the present disclosure can be used to evaluate the sensitization or the like of a hydrophilic sensitizer to a test substance in a manner that approximates the method of loading the test substance on the surface of a living body.

Example 6

Figure 11:
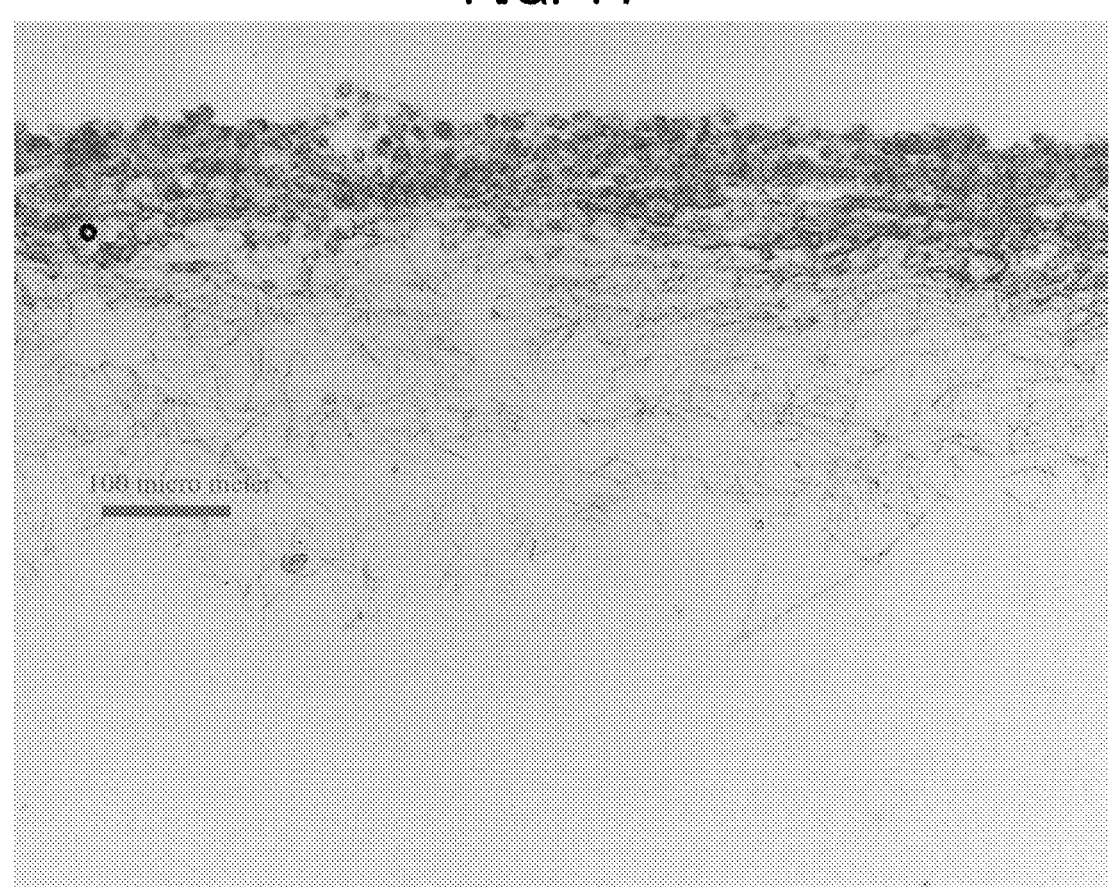
FIG. 11 is a diagram showing results of Example 6, showing a section of a three-dimensional culture after luminescence was measured for 72 hours by the real-time luminescence monitoring system for cultured cells in Example 5.

A three-dimensional culture was collected after the multicolor luminescence was measured for 72 hours in Example 5. The three-dimensional culture was stained with neutral red as in Example 1, and sections were cut lengthwise. This is shown in FIG. 11. It was confirmed that the three-dimensional culture was maintained after the multicolor luminescence measurement.

Example 7

The three-dimensional culture obtained in Example 3 was used to evaluate responses to dibutylaniline (DA) and hexyl salicylate (HS) as lipophilic sensitizers.

As in Example 5, a cell culture insert (Falcon Culture Insert #353095) comprising a clear, colorless, PET membrane with a 0.4 μm pore size bottom for 24 wells was inserted into the wells of a 24-well plate for cell culture with black walls and a colorless bottom, the three-dimensional culture was placed in the bottom of the culture insert with the cells on top, and 0.8 mL of KGM-gold containing 0.2 mM luciferin potassium salt was placed in the well outside the culture insert. For sensitization evaluation, a test substance was loaded from the top of the three-dimensional culture inside the insert. DA was diluted in olive oil to concentrations of 12.5% (v/v) and 25% (v/v), and 30 μL of the lysate was loaded from the top of the three-dimensional culture. HS was diluted in olive oil to a concentration of 12.5% (v/v) and 30 μL of the lysate was loaded from the top of the three-dimensional culture. As a solvent control, 30 μL of olive oil was added from the top of the three-dimensional culture. Plastic paraffin film was sprinkled around this well plate and the luminescence was measured for 0 to 72 hours with a real-time luminescence monitoring system for cultured cells, Kronos HT (manufactured by ATTO Corporation). Measurements were taken every minute for 10 seconds for each color and continued for 0 to 72 hours.

Figure 12:
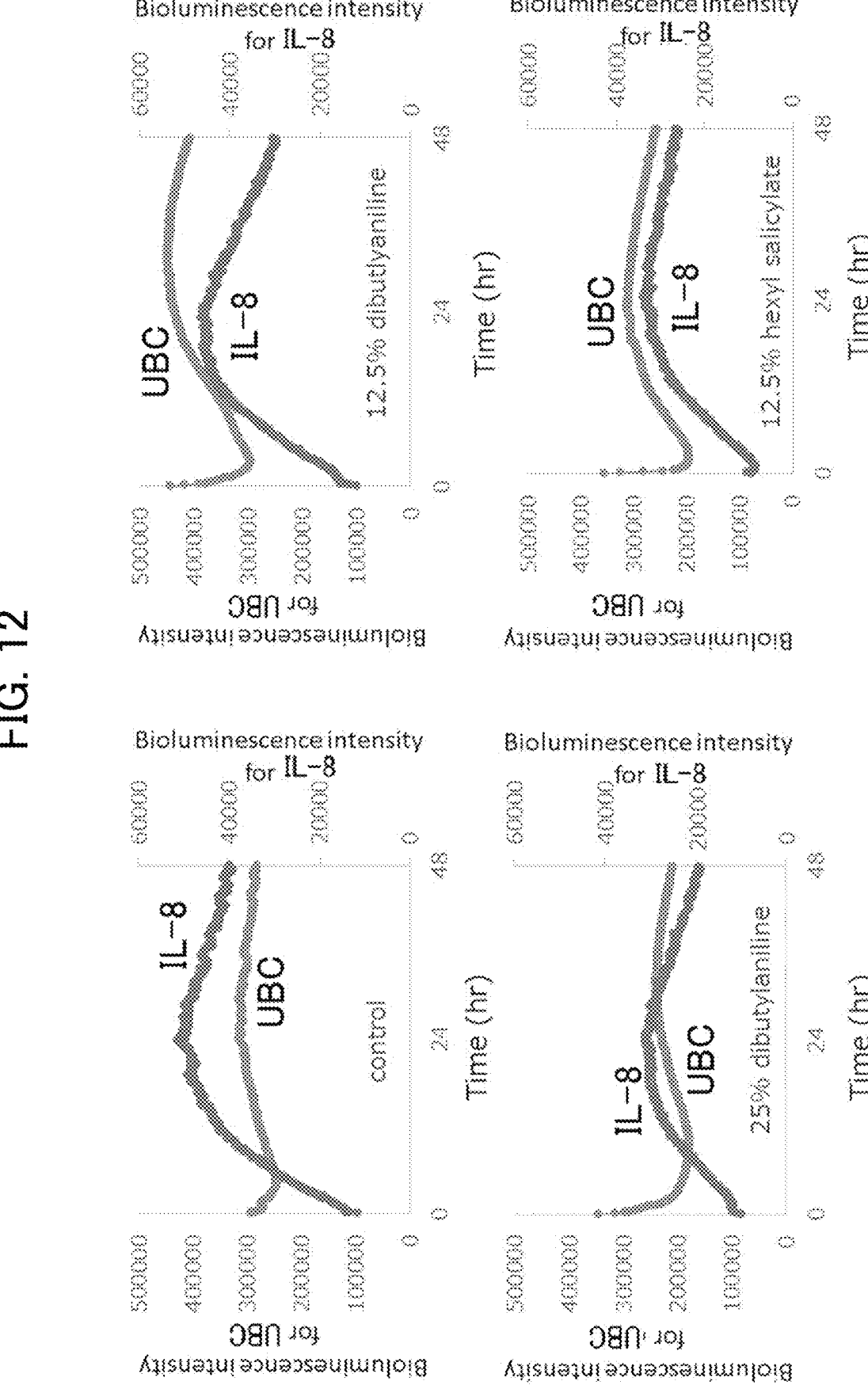
FIG. 12 is a diagram showing results of loading dibutylaniline (DA) and hexyl salicylate (HS) in Example 7, where the luminescence of red light-emitting luciferase and green light-emitting luciferase was measured for 48 hours by the real-time luminescence monitoring system for cultured cells.
Figure 13:
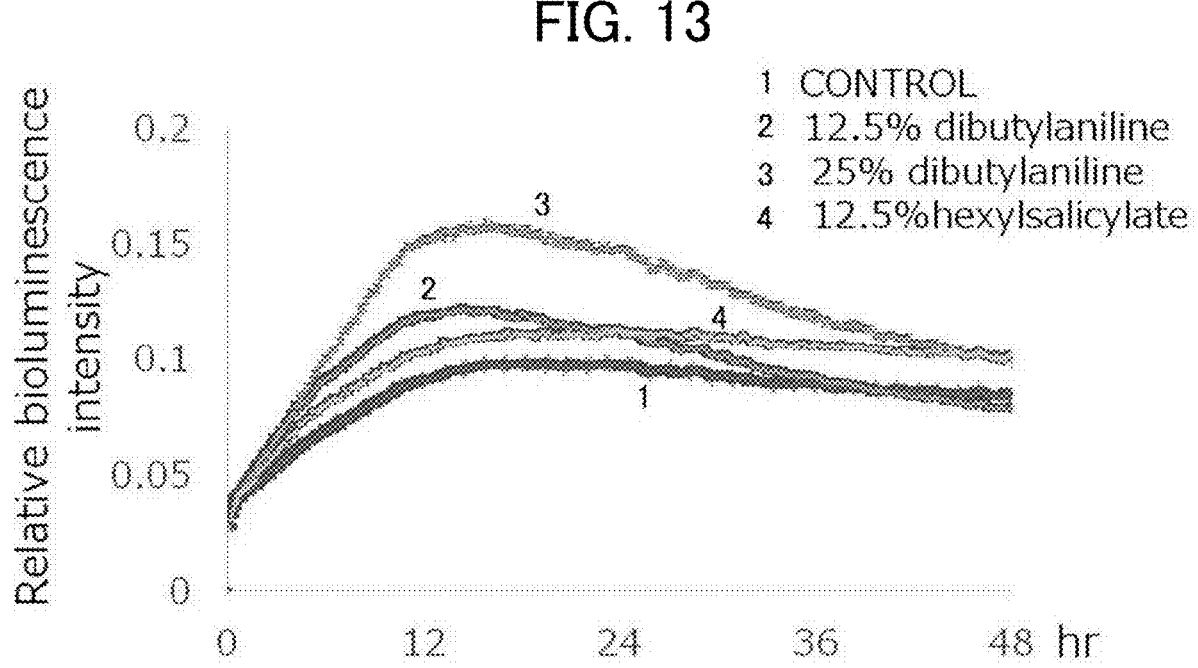
FIG. 13 is a diagram showing results of loading DA and HS in Example 7, showing the relative bioluminescence intensity of red light-emitting luciferase to green light-emitting luciferase.

FIG. 12 shows the red light-emitting luciferase (IL-8 promoter) luminescence and green light-emitting luciferase (ubiquitin C promoter) results for samples and controls loaded with various concentrations of solvent control, dibutylaniline, and hexylsalicylate up to 48 hours, and FIG. 13 shows the relative bioluminescence intensity of red light-emitting luciferase (IL-8 promoter) to green light-emitting luciferase (ubiquitin C promoter) in samples treated with various concentrations of the test substance and controls (plotted at each point mean+/−SD with n=3, respectively). As shown in FIG. 13, it was found that for any of the test substances, the IL-8/UBC ratio increased more than the solvent control by 24 hours, and the effect of the sensitizers was more pronounced than in a steady-state condition. A concentration dependence was observed for the emission intensity of DA. Since the superficial layer of the three-dimensional culture of the present disclosure comprises a stratum corneum, the sensitizing effect of a lipophilic substance can be evaluated in a short period of time. Moreover, as in Example 5, the method is similar to a sensitization test for evaluating allergic reactions in living bodies, in which a test substance is loaded from the top surface of a three-dimensional culture. It was found that the three-dimensional culture of the present disclosure can be used for sensitization evaluation in a manner similar to the method of loading a test substance on the surface of a living body, even with regard to lipophilicity.

Example 8

The three-dimensional culture obtained in Example 3 was used to evaluate the response to hydroquinone by loading hydroquinone from the bottom and top surfaces of the three-dimensional culture.

A cell culture insert (Falcon Culture Insert #353095) comprising a clear, colorless, PET membrane with a 0.4 μm pore size bottom for 24 wells was inserted into the wells of a 24-well plate for cell culture with black walls and a colorless bottom, the three-dimensional culture obtained in Example 3 was placed in the bottom of the culture insert with the cells on top. Culture media of 5 mL each were prepared by preparing KGM-gold containing 0.2 mM luciferin potassium salt and 25 mM HEPES-KOH (pH 7.5) and adding hydroquinone thereto at final concentrations of 20 μM, 100 μM, and 200 μM, respectively, in 5 mL each. 0.8 mL of this medium was placed on the outside of the culture insert, and then 30 μL was loaded from the top of the three-dimensional culture. 0.8 mL of KGM medium containing 0.2 mM luciferin potassium salt and 25 mM HEPES-KOH (pH 7.5) was added to a well as a solvent control, and 30 μL of KGM medium containing 0.2 mM luciferin potassium salt and 25 mM HEPES-KOH (pH 7.5) was loaded from the top of the three-dimensional culture. This added hydroquinone from the top and bottom surfaces of the three-dimensional culture.

Figure 14:
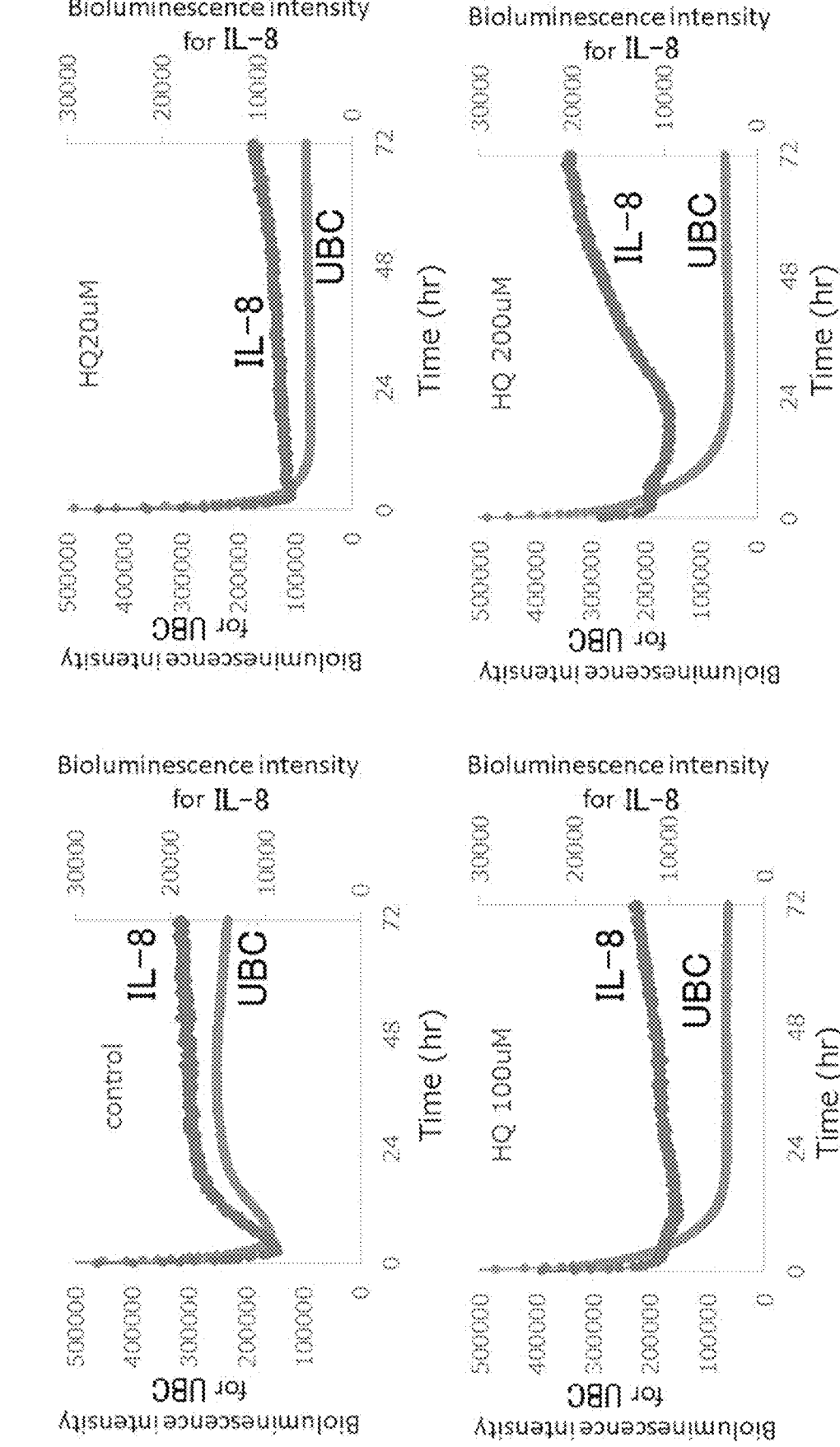
FIG. 14 is a diagram showing results of measuring the luminescence of red light-emitting luciferase and green light-emitting luciferase for 72 hours by the real-time luminescence monitoring system for cultured cells in Example 8.
Figure 15:
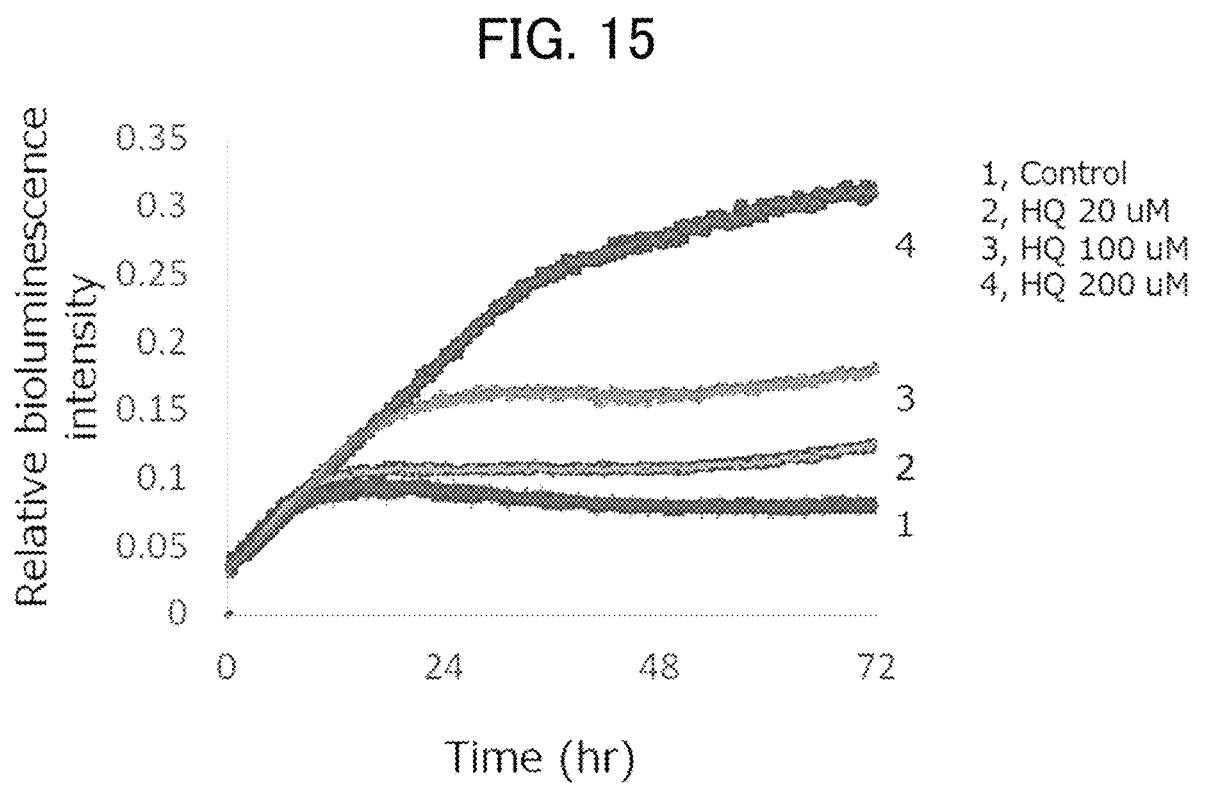

Plastic paraffin film was sprinkled around this well plate and the luminescence was measured for 0 to 72 hours with a real-time luminescence monitoring system for cultured cells, Kronos HT (manufactured by ATTO Corporation). The bioluminescence intensity of each luciferase was measured on these three-dimensional cultures as in Example 5. FIG. 14 shows the red light-emitting luciferase (IL-8 promoter) luminescence and green light-emitting luciferase (ubiquitin C promoter) results for samples and controls loaded with each concentration of HQ. FIG. 15 shows the biolumines-cence intensity ratio of red light-emitting luciferase (IL-8 promoter) to green light-emitting luciferase (ubiquitin C promoter) in samples loaded with various concentrations of the test substance and controls (plotted at each point mean+/−SD with n=3, respectively).

As shown in FIG. 15, the bioluminescence intensity ratio increased in a concentration-dependent manner for HQ. Comparing FIG. 10, where the test substance was adminis-tered only from the top surface of the three-dimensional culture, with FIG. 15, where the test substance was admin-istered to the three-dimensional culture from both the bot-tom and top surfaces of the wells, it was found that sensi-tization could be detected even at low concentrations when the test substance was administered from both the bottom and the top surfaces of the wells.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

---

The invention claimed is:

1. A method for producing a three-dimensional culture of HaCaT cells with stratum corneum formed on a superficial layer thereof, the method comprising:

performing three-dimensional culture of HaCaT cells including a gene of first luciferase controlled by a stable expression promoter and a gene of second luciferase controlled by a promoter that is capable of evaluating skin sensitization, with enough culture medium not to dry out a superficial layer of a HaCaT cell layer formed by layering of the HaCaT cells, signals from the first luciferase and the second luciferase being detected distinguishably from each other.

2. The method for producing according to claim 1, further comprising:

seeding the HaCaT cells on a top surface of a plate-like substrate, wherein the three-dimensional culture of the HaCaT cells is performed with enough culture medium not to dry out the superficial layer of the HaCaT cell layer.

3. The method for producing according to claim 2, further comprising:

storing an inner container in an outer container, the inner container including the plate-like substrate on a bottom thereof, wherein the three-dimensional culture of the HaCaT cells is performed with enough culture medium not to dry out the superficial layer of the HaCaT cell layer being charged in the outer container.

4. The method for producing according to claim 1, wherein the HaCaT cells further include a gene of third luciferase controlled by a promoter that is capable of evaluating physiological activity, a signal from the third luciferase being detected distinguishably from either of the signals from the first luciferase and the second luciferase.

* * * * *